US011631172B2

(12) United States Patent
Liu

(10) Patent No.: US 11,631,172 B2
(45) Date of Patent: Apr. 18, 2023

(54) METHODS AND APPARATUSES FOR GUIDING COLLECTION OF ULTRASOUND IMAGES

(71) Applicant: BFLY OPERATIONS, INC., Burlington, MA (US)

(72) Inventor: Yang Liu, Hoboken, NJ (US)

(73) Assignee: BFLY OPERATIONS, INC., Burlington, MA (US)

(*) Notice: Subject to any disclaimer, the term of this patent is extended or adjusted under 35 U.S.C. 154(b) by 168 days.

(21) Appl. No.: 16/839,020

(22) Filed: Apr. 2, 2020

(65) Prior Publication Data

US 2020/0320695 A1 Oct. 8, 2020

Related U.S. Application Data

(60) Provisional application No. 62/828,726, filed on Apr. 3, 2019.

(51) Int. Cl.
| | |
|---|---|
| *A61B 8/00* | (2006.01) |
| *A61B 8/08* | (2006.01) |
| *G06T 7/00* | (2017.01) |
| *G06T 7/11* | (2017.01) |
| *G06T 7/143* | (2017.01) |
| *G06T 7/73* | (2017.01) |

(52) U.S. Cl.
CPC ............ *G06T 7/0012* (2013.01); *A61B 8/085* (2013.01); *A61B 8/463* (2013.01); *G06T 7/73* (2017.01); *G06T 2207/10132* (2013.01); *G06T 2207/30004* (2013.01)

(58) Field of Classification Search
None
See application file for complete search history.

(56) References Cited

U.S. PATENT DOCUMENTS

| | | |
|---|---|---|
| 2007/0103464 A1 | 5/2007 | Kaufman et al. |
| 2008/0205717 A1 | 8/2008 | Reeves et al. |
| | (Continued) | |

FOREIGN PATENT DOCUMENTS

| | | |
|---|---|---|
| WO | WO 2017/222964 A1 | 12/2017 |
| WO | WO 2017/222970 A1 | 12/2017 |

OTHER PUBLICATIONS

International Search Report and Written Opinion dated Jun. 25, 2020 in connection with International Application No. PCT/US2020/026318.

*Primary Examiner* — Soo Shin
(74) *Attorney, Agent, or Firm* — Carter, DeLuca & Farrell LLP

(57) ABSTRACT

Aspects of the technology described herein relate to receiving an ultrasound image, automatically determining a location of a specific point on an anatomical structure depicted in the ultrasound image, and displaying an indicator of the location of the specific point on the anatomical structure on the ultrasound image. In some embodiments, the anatomical structure is a bladder. In some embodiments, the specific point is the centroid. In some embodiments, a statistical model determines the specific point. The indicator may be, for example, a symbol located at the specific point, a horizontal line extending through the specific point from one edge of the anatomical structure to another, and/or a vertical line extending through the specific point from one edge of the anatomical structure to another.

22 Claims, 18 Drawing Sheets

(56) References Cited

U.S. PATENT DOCUMENTS

| | | | |
|---|---|---|---|
| 2009/0112089 A1* | 4/2009 | Barnard | A61B 8/483 |
| | | | 600/443 |
| 2009/0264757 A1* | 10/2009 | Yang | G01S 7/52082 |
| | | | 600/443 |
| 2010/0036252 A1* | 2/2010 | Chalana | G01S 7/52036 |
| | | | 600/449 |
| 2010/0069756 A1* | 3/2010 | Ogasawara | A61B 8/08 |
| | | | 600/447 |
| 2011/0055447 A1 | 3/2011 | Costa | |
| 2015/0238276 A1* | 8/2015 | Atarot | A61B 17/00234 |
| | | | 606/130 |
| 2017/0164924 A1* | 6/2017 | Urabe | A61B 8/5223 |
| 2017/0360397 A1 | 12/2017 | Rothberg et al. | |
| 2017/0360401 A1 | 12/2017 | Rothberg et al. | |
| 2021/0007710 A1* | 1/2021 | Douglas | A61B 8/4245 |
| 2021/0330296 A1* | 10/2021 | Silberman | G06N 20/00 |
| 2022/0056534 A1* | 2/2022 | Rivers | C12Q 1/6869 |

* cited by examiner

METHODS AND APPARATUSES FOR GUIDING COLLECTION OF ULTRASOUND IMAGES

CROSS-REFERENCE TO RELATED APPLICATIONS

The present application claims the benefit under 35 U.S.C. § 119(e) of U.S. Provisional Patent Application Ser. No. 62/828,726, filed Apr. 3, 2019, and entitled "METHODS AND APPARATUSES FOR GUIDING COLLECTION OF ULTRASOUND IMAGES," which is hereby incorporated herein by reference in its entirety.

FIELD

Generally, the aspects of the technology described herein relate to collection of ultrasound images.

BACKGROUND

Ultrasound probes may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect, an apparatus includes processing circuitry configured to receive an ultrasound image, determine a location of a specific point on an anatomical structure depicted in the ultrasound image, and display an indicator of the location of the specific point on the anatomical structure on the ultrasound image.

In some embodiments, the anatomical structure comprises a bladder. In some embodiments, the processing circuitry is configured, when determining the location of the specific point on the anatomical structure depicted in the ultrasound image, to use a statistical model. In some embodiments, the specific point on the anatomical structure has predetermined mathematical characteristics. In some embodiments, the processing circuitry is configured, when automatically determining the location of the specific point on the anatomical structure depicted in the ultrasound image, to use a mathematical formula or algorithm. In some embodiments, the processing circuitry is configured, when determining the location of the specific point on the anatomical structure depicted in the ultrasound image, to determine a centroid of the anatomical structure depicted in the ultrasound image. In some embodiments, the processing circuitry is configured, when determining the location of the specific point on the anatomical structure depicted in the ultrasound image to determine a point on the anatomical structure that is farthest from all the edge points of the anatomical structure.

In some embodiments, the processing circuitry is configured, when displaying the indicator of the location of the specific point on the anatomical structure on the ultrasound image, to display a symbol located at the specific point on the anatomical structure on the ultrasound image. In some embodiments, the processing circuitry is configured, when displaying the indicator of the location of the specific point on the anatomical structure on the ultrasound image, to display a vertical line extending from one edge of the anatomical structure, through the specific point on the anatomical structure, and to the other edge of the anatomical structure. In some embodiments, the processing circuitry is configured, when displaying the indicator of the location of the specific point on the anatomical structure on the ultrasound, to display a horizontal line extending from one edge of the anatomical structure, through the specific point on the anatomical structure, and to the other edge of the anatomical structure.

In some embodiments, the processing circuitry is further configured to display a second indicator when the indicator is within a threshold distance of either or both of a vertical line positioned halfway across a horizontal dimension of the ultrasound image and a horizontal line positioned halfway across a vertical dimension of the ultrasound image. In some embodiments, the processing circuitry is further configured to display a second indicator indicating indicate how close the indicator is to either or both of a vertical line positioned halfway across a horizontal dimension of the ultrasound image and a horizontal line positioned halfway across a vertical dimension of the ultrasound image. In some embodiments, the processing circuitry is further configured to display no other indicators of locations on the anatomical structure.

Some aspects include at least one non-transitory computer-readable storage medium storing processor-executable instructions that, when executed by at least one processor, cause the at least one processor to perform the above aspects and embodiments. Some aspects include a method to perform the actions that the processing device is configured to perform.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1:
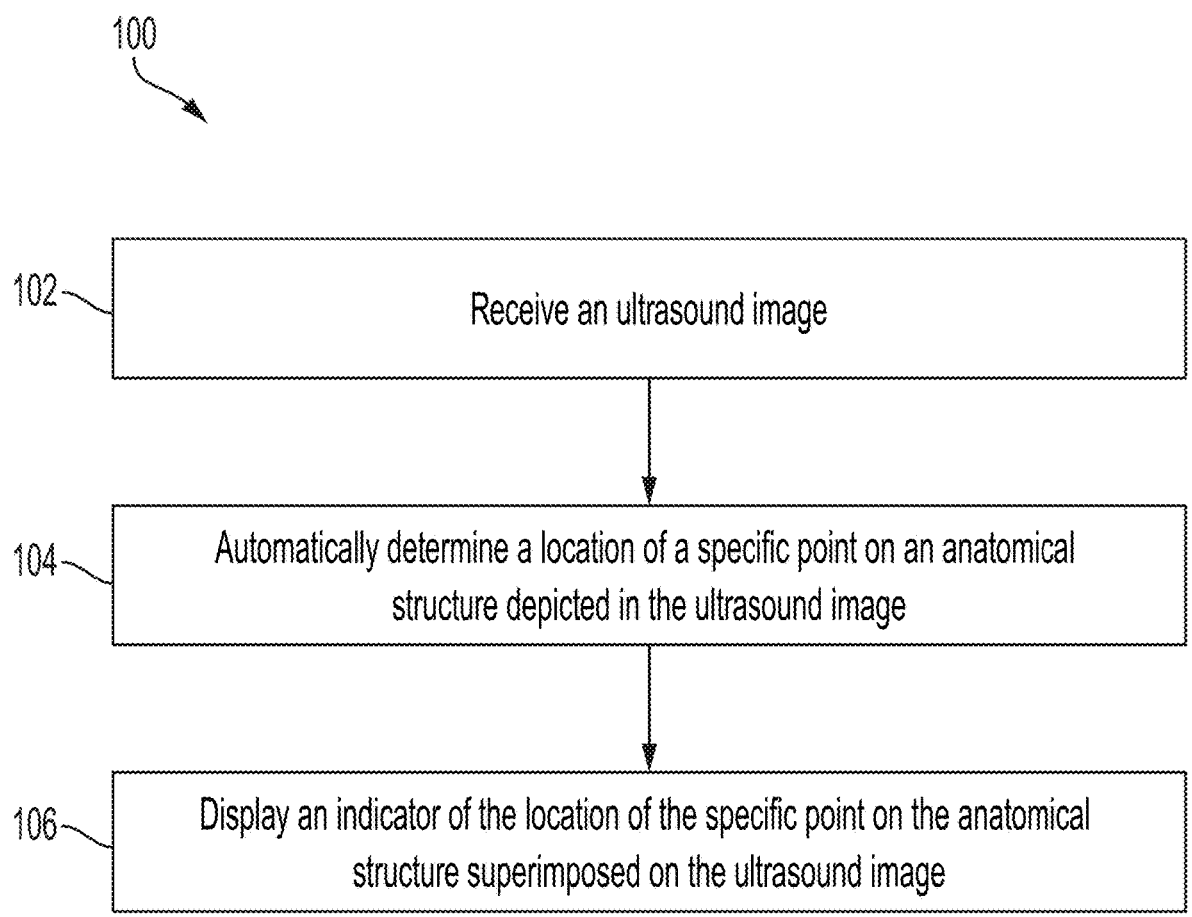
FIG. 1 illustrates a process for collection of an ultrasound image of an anatomical structure, in accordance with certain embodiments described herein.

Some applications of ultrasound imaging include capturing one or more ultrasound images of an anatomical structure (e.g., a bladder) and performing a clinical calculation based on the one or more ultrasound images. For example, after capturing one or more ultrasound images of a bladder, the volume of the bladder may be calculated. In some applications, it may be helpful to position an ultrasound device capturing an ultrasound image such that the anatomical structure is centered with respect to the horizontal and/or vertical dimensions of the ultrasound image. This may help improve the accuracy of calculations performed based on the anatomical structure in the ultrasound image, as image quality may be better in the center of an ultrasound image. Additionally, centering the anatomical structure may help to minimize the chance that a portion of the anatomical structure will be clipped at the edge of the ultrasound image.

In some embodiments, a processing device displaying ultrasound images collected by an ultrasound device may display a vertical line positioned halfway across the horizontal dimension of the ultrasound image and/or a horizontal line positioned halfway across the vertical dimension of the ultrasound image. The inventors have recognized that it may also be helpful for the processing device to display an indicator of a specific point on an anatomical structure in an ultrasound image. For example, the specific point may be the centroid of the anatomical structure in an ultrasound image. As another example, the specific point may be the point on the anatomical structure that is farthest from all the edge points of the anatomical structure. It should be appreciated that other points on the anatomical structure may be used as well. Examples of indicators include a symbol positioned at the specific portion on the anatomical structure and/or a line extending horizontally or vertically from one edge of the anatomical structure, through the specific point on the anatomical structure, and to the other edge of the anatomical structure. In some embodiments, the processing device may use a statistical model to determine the location of the specific point on the anatomical structure in an ultrasound image. As the ultrasound device collects more ultrasound images that are displayed the processing device, and the anatomical structure is located at different locations on the ultrasound image, the processing device may reposition the indicator such that the indicator continues to be located at the specific point on the anatomical structure.

Displaying the indicator may help the user to position the ultrasound device such that the anatomical structure is centered in the ultrasound image. As the user moves the ultrasound device, the position of the anatomical structure in the ultrasound image may change. When the anatomical structure is positioned in the ultrasound image such that the indicator is positioned within a threshold distance of the vertical line positioned halfway across the horizontal dimension of the ultrasound image and/or within a threshold distance of the horizontal line positioned halfway across the vertical dimension of the ultrasound image, this may indicate that the anatomical structure is centered with respect to the horizontal and/or vertical dimension of the ultrasound image.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIG. 1 illustrates a process 100 for collection of an ultrasound image of an anatomical structure, in accordance with certain embodiments described herein. The process 100 is performed by a processing device in operative communication with an ultrasound device. The processing device may be, for example, a mobile phone, tablet, or laptop in operative communication with an ultrasound device. The ultrasound device and the processing device may communicate over a wired communication link (e.g., over Ethernet, a Universal Serial Bus (USB) cable or a Lightning cable) or over a wireless communication link (e.g., over a BLUETOOTH®, WiFi, or ZIGBEE wireless communication link). In some embodiments, the ultrasound device itself may perform the process 100.

In act 102, the processing device receives an ultrasound image. The ultrasound image may be generated based on raw ultrasound data collected by the ultrasound device. In some embodiments, the ultrasound device may generate the ultrasound image based on the raw ultrasound data, and at act 102, the processing device may receive the ultrasound image from the ultrasound device. In some embodiments, the ultrasound device may generate scan lines from the raw ultrasound data, and at act 102, the processing device may receive the scan lines from the ultrasound device and generate the ultrasound image based on the scan lines. In some embodiments, at act 102, the processing device may receive the raw ultrasound data from the ultrasound device and generate the ultrasound image based on the raw ultrasound data. The ultrasound image may be the most recently collected ultrasound image by the ultrasound device, and the processing device may receive the ultrasound image in real-time, as it is collected. The process 100 proceeds from act 102 to act 104.

In act 104, the processing device automatically determines a location of a specific point on an anatomical structure depicted in the ultrasound image. For example, the anatomical structure may be the bladder. In some embodiments, the specific point may have predetermined mathematical characteristics. In some embodiments, determining the specific point may include using a mathematical formula or algorithm. Examples of the specific point include the centroid of the anatomical structure and the point on the anatomical structure that is farthest from all the edge points of the anatomical structure, although other specific points may be used. In some embodiments, a statistical model may be trained to automatically determine the location of a specific point on an anatomical structure depicted in an ultrasound image. The statistical model may be stored on the processing device or stored on another electronic device (e.g., a server) and accessed by the processing device.

For the example where the specific point is the centroid of the anatomical structure, in some embodiments, the statistical model may be trained on multiple pairs of input and output training data sets as a segmentation model. Each set of input training data may be an ultrasound image depicting an anatomical structure. Each set of output training data may be a segmentation mask that is an array of values equal in size to the input training data ultrasound image, and pixels corresponding to locations within the anatomical structure in the ultrasound image are manually set to 1 and other pixels are set to 0. Based on this training data, the statistical model may learn to output, based on an inputted ultrasound image, a segmentation mask where each pixel has a value representing the probability that the pixel corresponds to a location within the anatomical structure in the ultrasound image (values closer to 1) or outside the anatomical structure (values closer to 0). The processing device may select all pixels in the segmentation mask that have a value greater than a threshold value (e.g., 0.5) as being within the anatomical structure. To determine the location of the centroid of the anatomical structure depicted in the ultrasound image, the processing device may calculate the arithmetic mean of all the locations of pixels that were determined to be within the anatomical structure. For example, the processing device may calculate the arithmetic mean of the horizontal locations of all pixels within the anatomical structure and the arithmetic mean of the vertical locations of all pixels within the anatomical structure. The processing device may determine the location of the centroid of the anatomical structure to be the pixel having a horizontal position that is at the arithmetic mean of all pixels within the anatomical structure and having a vertical position that is at the arithmetic mean of all pixels within the anatomical structure.

In some embodiments, the statistical model may be trained on multiple pairs of input and output training data sets as a keypoint localization model. Each set of input training data may be an ultrasound image depicting an anatomical structure. Each set of output training data may be an array of values that is the same size as the input training data ultrasound image, where the pixel corresponding to the centroid of the anatomical structure in the ultrasound image is manually set to a value of 1 and every other pixel has a value of 0. Based on this training data, the statistical model may learn to output, based on an inputted ultrasound image, an array of values that is the same size as the inputted image, where each pixel in the array consists of a probability that that pixel is where the centroid of an anatomical structure depicted in the ultrasound image is located. The processing device may select the pixel having the highest probability as the location of the specific point on the anatomical structure in the ultrasound image.

In some embodiments, the statistical model may be trained on multiple pairs of input and output training data sets to use regression. Each set of input training data may be an ultrasound image depicting an anatomical structure. Each set of output training data set may be the pixel location of the centroid of the anatomical structure in the input training data ultrasound image. Based on this training data, the statistical model may learn to output, based on an inputted ultrasound image, the horizontal and vertical pixel coordinates of the centroid of an anatomical structure depicted in the ultrasound device.

For the example where the specific point is the point on the anatomical structure that is farthest from all the edge points of the anatomical structure, in some embodiments, the statistical model may be trained on multiple pairs of input and output training data sets as a segmentation model. Each set of input training data may be an ultrasound image depicting an anatomical structure. Each set of output training data may be a segmentation mask that is an array of values equal in size to the input training data ultrasound image, and pixels corresponding to locations on the boundary of the anatomical structure in the ultrasound image are manually set to 1 and other pixels are set to 0. Based on this training data, the statistical model may learn to output, based on an inputted ultrasound image, a segmentation mask where each pixel has a value representing the probability that the pixel corresponds to a boundary of the anatomical structure in the ultrasound image (values closer to 1) or does not correspond to a boundary of the anatomical structure (values closer to 0). The processing device may select all pixels in the segmentation mask that have a value greater than a threshold value (e.g., 0.5) as being on the boundary of the anatomical structure. To determine the location of the point on the anatomical structure that is farthest from all the edge points of the anatomical structure depicted in the ultrasound image, the processing device may calculate, for every pixel inside the boundary, the sum of the distances of that pixel to every pixel on the boundary. The processing device may then select the pixel having the greater sum of distances as the location of the specific point on the anatomical structure in the ultrasound image.

In some embodiments, the statistical model may be trained on multiple pairs of input and output training data sets as a keypoint localization model. Each set of input training data may be an ultrasound image depicting an anatomical structure. Each set of output training data may be an array of values that is the same size as the input training data ultrasound image, where the pixel corresponding to the point on the anatomical structure that is farthest from all the edge points of the anatomical structure in the ultrasound image is manually set to a value of 1 and every other pixel has a value of 0. Based on this training data, the statistical model may learn to output, based on an inputted ultrasound image, an array of values that is the same size as the inputted image, where each pixel in the array consists of a probability that that pixel is where the point on the anatomical structure that is farthest from all the edge points of the anatomical structure in the ultrasound image is located. The processing device may select the pixel having the highest probability as the location of the specific point on the anatomical structure in the ultrasound image.

In some embodiments, the statistical model may be trained on multiple pairs of input and output training data sets to use regression. Each set of input training data may be an ultrasound image depicting an anatomical structure. Each set of output training data set may be the pixel location of the point on the anatomical structure that is farthest from all the edge points of the anatomical structure. Based on this training data, the statistical model may learn to output, based on an inputted ultrasound image, the horizontal and vertical pixel coordinates of the point on the anatomical structure that is farthest from all the edge points of the anatomical structure. The process 100 proceeds from act 104 to act 106.

In act 106, the processing device displays the ultrasound image (received in act 102) and an indicator of the location of the specific point on the anatomical structure (determined in act 104) superimposed on the ultrasound image. The processing device may display the ultrasound image on a display screen of the processing device. The indicator of the location of the specific point on the anatomical structure may include a symbol (e.g., a box, a rounded box, a circle, an "x", a crosshairs, etc.) and may be located at the location of the specific point on the anatomical structure. For example, one of the pixels of the symbol may be at the location of the specific point on the anatomical structure in the ultrasound image (or is the pixel closest to this location). The symbol may be centered at the location of the specific point, or the center of the symbol may be at the pixel which is closest to this location. In some embodiments, the indicator of the location of the specific point on the anatomical structure may not be located at the location of the specific point, but at a location that is based on the location of the specific point (e.g., a certain number of pixels away from the specific point in a particular direction). In some embodiments, only one indicator (namely, the indicator of the location of the specific point on the anatomical structure) may be displayed on the anatomical structure, and no other indicators of locations on the anatomical structure may be displayed.

In some embodiments, the indicator may include a vertical line extending from one edge of the anatomical structure, through the specific point on the anatomical structure, to the other edge of the anatomical structure. In some embodiments, the indicator may include a horizontal line extending from one edge of the anatomical structure, through the specific point on the anatomical structure, and to the other edge of the anatomical structure. In some embodiments, the indicator may include two or more of a symbol at the specific point on the anatomical structure, a horizontal line extending through the specific point, and a vertical line extending through the specific point. In some embodiments, to position such vertical lines or horizontal lines, the processing device may use a segmentation mask for the anatomical structure that is returned by a statistical model, where the segmentation mask indicates the boundary of the anatomical structure (as described above). Thus, by using the location of the specific point on the anatomical structure and the boundary of the anatomical structure, the processing device may determine how to position a vertical or horizontal line extending from one edge of the anatomical structure, through the specific point on the anatomical structure, and to the other edge of the anatomical structure.

FIGS. 2-17 illustrate example graphical user interfaces (GUIs) for collection of ultrasound images of an anatomical structure, in accordance with certain embodiments described herein. The GUIs may be displayed by a processing device in operative communication with an ultrasound device. The processing device may be, for example, a mobile phone, tablet, or laptop in operative communication with an ultrasound device. The ultrasound device and the processing device may communicate over a wired communication link (e.g., over Ethernet, a Universal Serial Bus (USB) cable or a Lightning cable) or over a wireless communication link (e.g., over a BLUETOOTH®, WiFi, or ZIGBEE wireless communication link). In some embodiments, the ultrasound device itself may display the GUIs.

Figure 2:
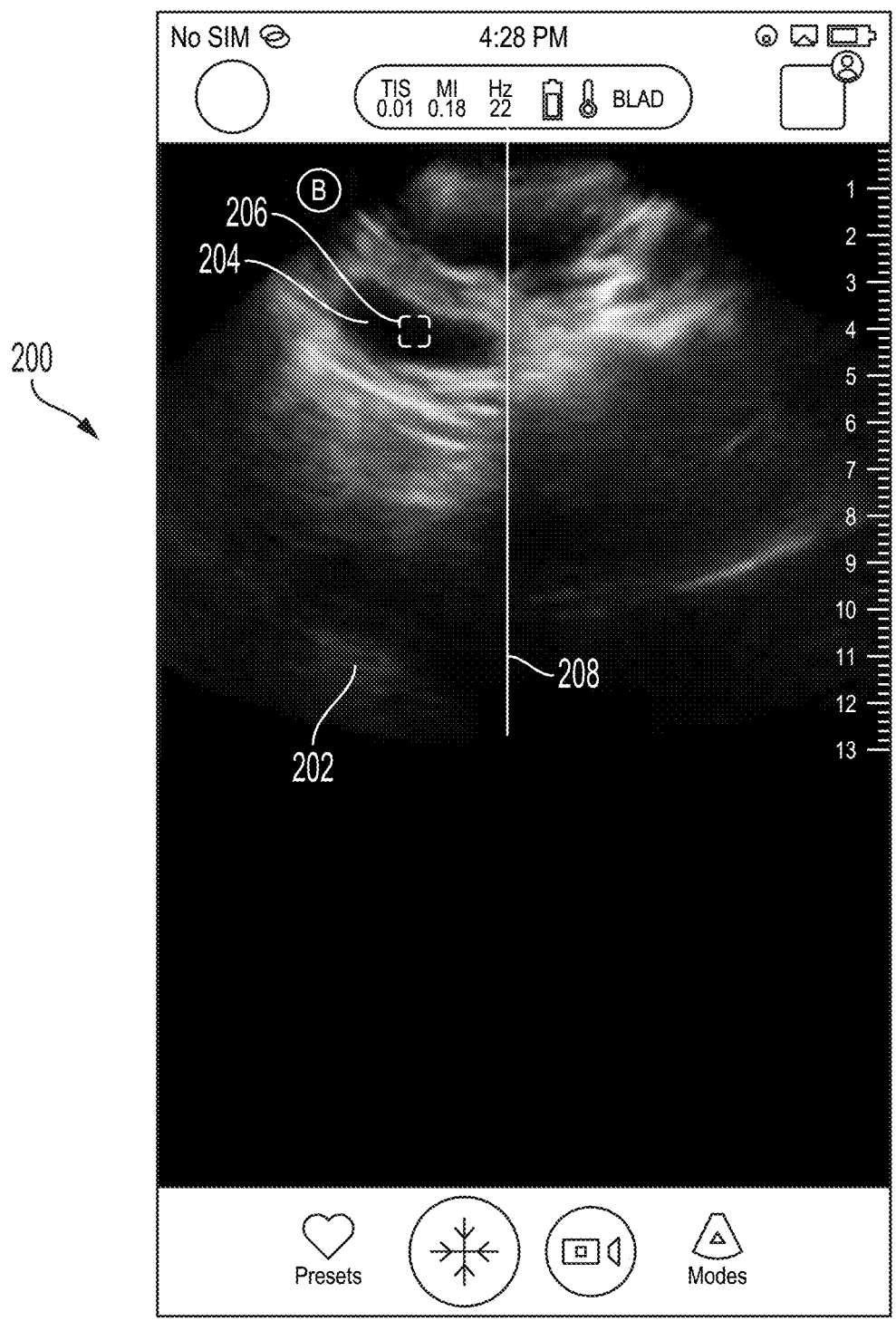
FIG. 2 illustrates an example graphical user interface (GUI) for collection of ultrasound images of an anatomical structure, in accordance with certain embodiments described herein.

FIG. 2 illustrates an example GUI 200, in accordance with certain embodiments described herein. The GUI 200 includes an ultrasound image 202, a symbol 206, and a vertical line 208. The ultrasound image 202 depicts an anatomical structure 204. In FIG. 1 and the other figures included herein, the ultrasound images are shown in black and white. Those colors may be reversed in practice, meaning that regions shown in white may alternatively be shown in black, and vice versa.

In FIG. 2, the anatomical structure 204 is a bladder, but may be another anatomical structure as well. Further description of the ultrasound image 202 may be found with reference to act 102. The symbol 206 is superimposed on the ultrasound image 202 and is an indicator of the location of a specific point on the anatomical structure 204. In FIG. 2, the symbol 206 is an indicator of the location of the centroid of the anatomical structure 204. The symbol 206 is a rounded box, but in some embodiments other symbols (e.g., crosshairs, an "x" or a circle) may be used. The use of a box, rounded box, or circle may allow for greater flexibility in positioning the symbol 206 relative to the vertical line 208, whereas the use of crosshairs may prompt the user to seek greater precision in the positioning of symbol 206. Further description of the symbol 206 may be found with reference to acts 104 and 106. As the ultrasound device collects new ultrasound images that are displayed by the processing device, and the anatomical structure 204 is located at different locations on the ultrasound image 202, the processing device may reposition the symbol 206 such that the symbol 206 continues to be located at the centroid of the anatomical structure 204. The vertical line 208 extends vertically (i.e., vertically with respect to the ultrasound image 202) through the ultrasound image 202 and is located halfway along the horizontal dimension of the ultrasound image 202. In FIG. 2, the vertical line 208 extends all the way through the ultrasound image 202, but in some embodiments the vertical line 208 may extend through only a portion of the ultrasound image 202. The vertical line is shown as solid, but may be dashed in some embodiments.

Displaying the symbol 206 may help the user position the ultrasound device such that the anatomical structure 204 is centered in the ultrasound image 202. As the user moves the ultrasound device, the position of the anatomical structure 204 in the ultrasound image 202 may change. Because in FIG. 2, the anatomical structure 204 is not positioned in the ultrasound image 202 such that the symbol 206 is positioned within a threshold distance of the vertical line 208, this may indicate that the anatomical structure 204 is not centered with respect to the horizontal dimension of the ultrasound image 202.

Figure 3:
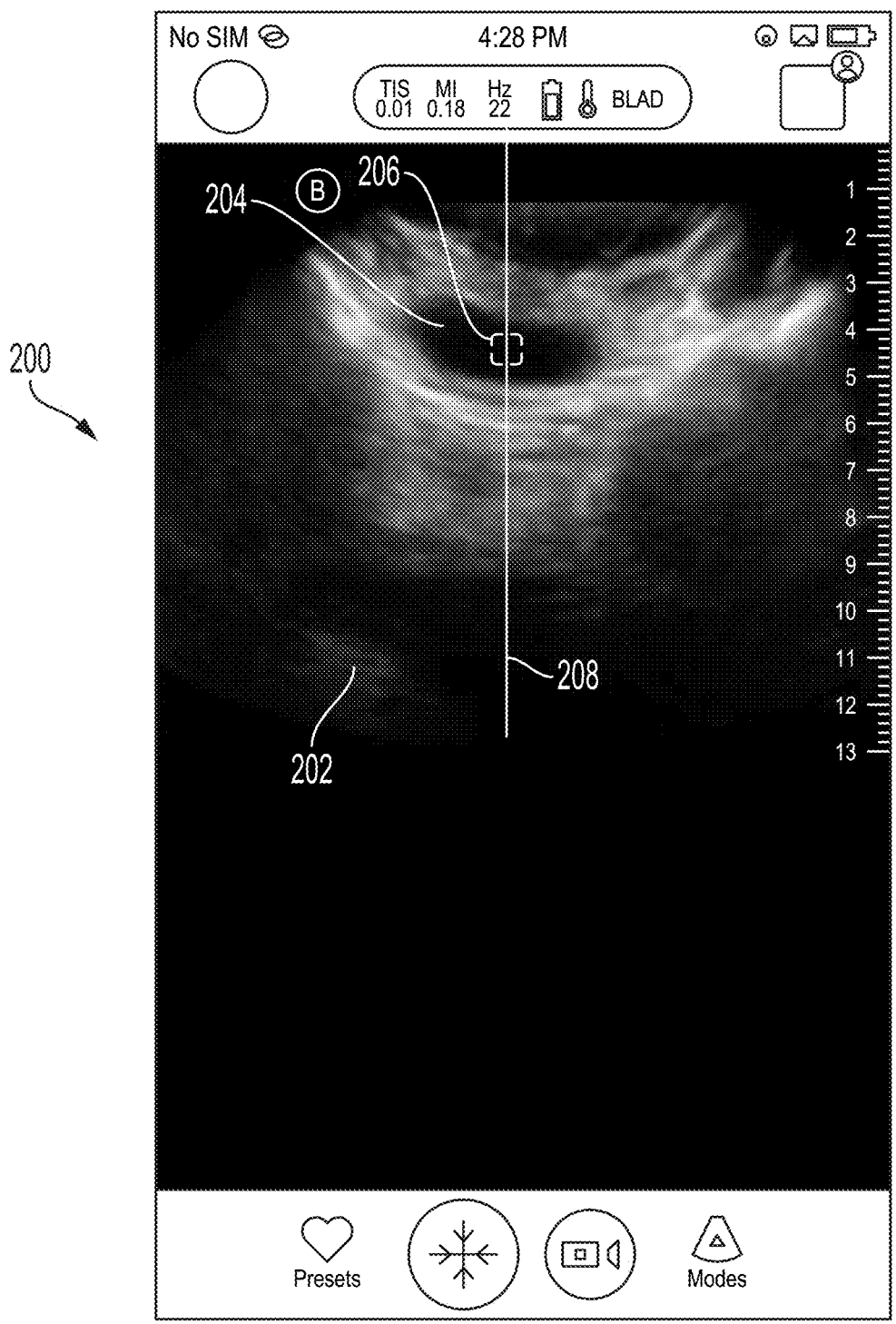
FIG. 3 illustrates another example of the GUI of FIG. 2, in accordance with certain embodiments described herein.

FIG. 3 illustrates another example of the GUI 200, in accordance with certain embodiments described herein. In FIG. 3, the anatomical structure 204 is positioned in the ultrasound image 202 such that the symbol 206 is positioned within a threshold distance of the vertical line 208. This may indicate that the anatomical structure 204 is centered with respect to the horizontal dimension of the ultrasound image 202.

Figure 4:
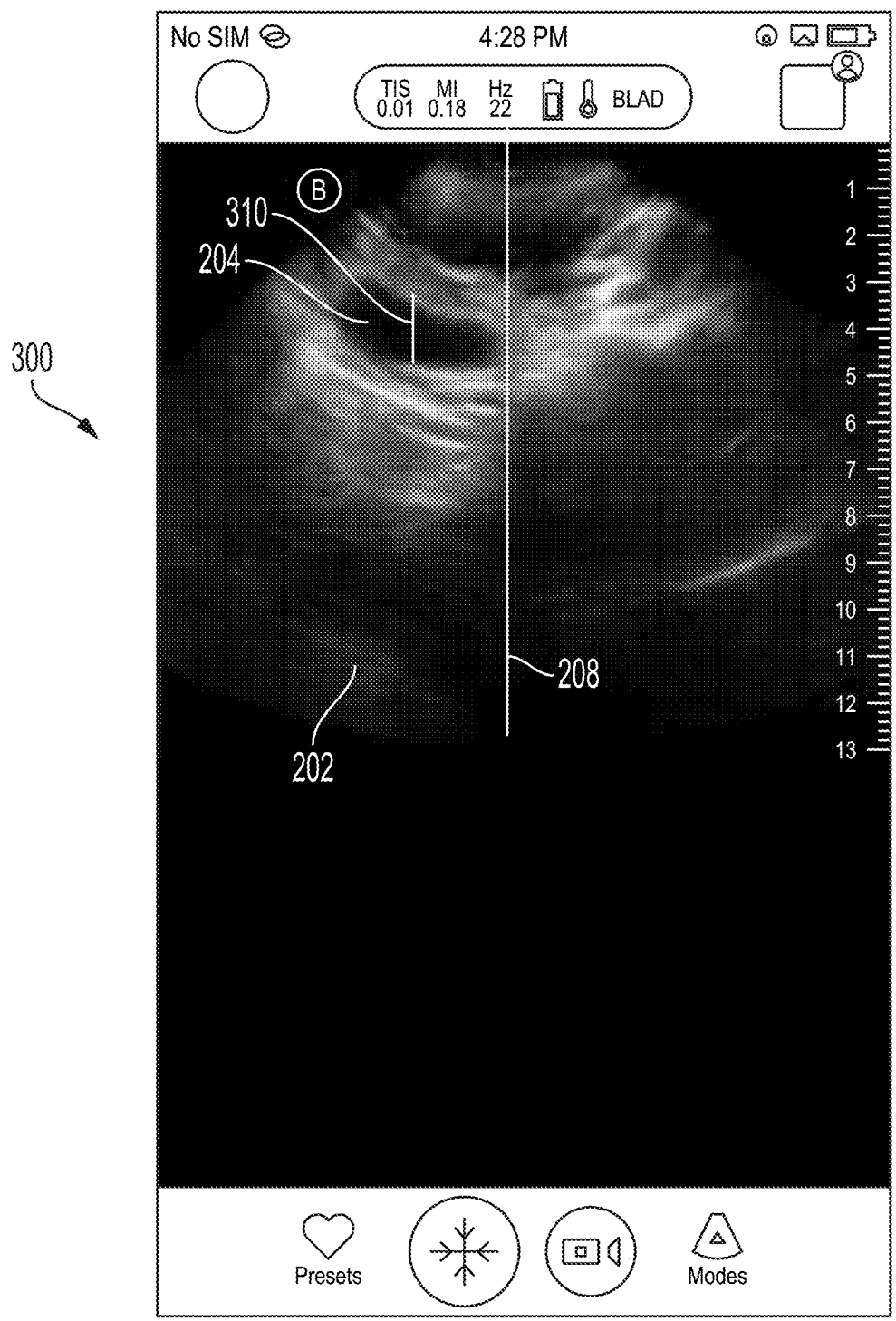
FIG. 4 illustrates another example graphical user interface (GUI) for collection of ultrasound images of an anatomical structure, in accordance with certain embodiments described herein.

FIG. 4 illustrates another example GUI 300, in accordance with certain embodiments described herein. The GUI 300 is the same as the GUI 200, except that the GUI 300 includes a vertical line 310 and lacks the symbol 206. The vertical line 310 is superimposed on the ultrasound image 202 and is an indicator of the location of a specific point on the anatomical structure 204. In FIG. 4, the vertical line 310 is an indicator of the location of the centroid of the anatomical structure 204. In particular, the vertical line 310 extends vertically (i.e., vertically with respect to the ultrasound image 202) from one edge of the anatomical structure 204, through the location of the centroid of the anatomical structure 204, and to the other edge of the anatomical structure 204. As the ultrasound device collects new ultrasound images that are displayed by the processing device, and the anatomical structure 204 is located at different locations on the ultrasound image 202, the processing device may reposition the vertical line 310 such that the vertical line 310 continues to extend vertically from one edge of the anatomical structure 204, through the location of the centroid of the anatomical structure 204, and to the other edge of the anatomical structure 204. Further description of the vertical line 310 may be found with reference to acts 104 and 106.

Displaying the vertical line 310 may help the user position the ultrasound device such that the anatomical structure 204 is centered in the ultrasound image 202. As the user moves the ultrasound device, the position of the anatomical structure 204 in the ultrasound image 202 may change. Because in FIG. 4, the anatomical structure 204 is not positioned in the ultrasound image 202 such that the vertical line 310 is positioned within a threshold distance of the vertical line 208, this may indicate that the anatomical structure 204 is not centered with respect to the horizontal dimension of the ultrasound image 202.

Figure 5:
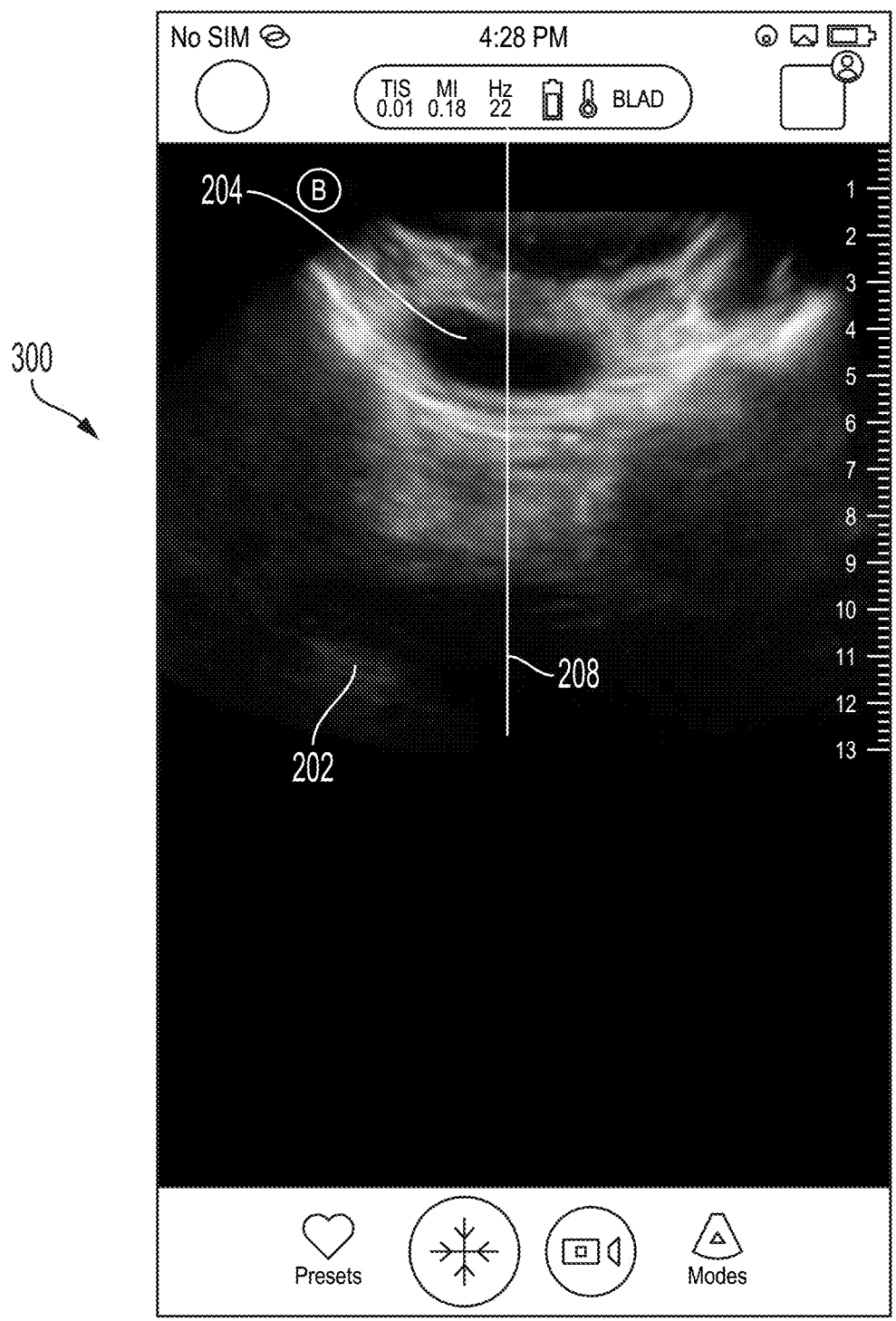
FIG. 5 illustrates another example of the GUI of FIG. 4, in accordance with certain embodiments described herein.

FIG. 5 illustrates another example of the GUI 300, in accordance with certain embodiments described herein. In FIG. 5, the anatomical structure 204 is positioned in the ultrasound image 202 such that the vertical line 310 is positioned within a threshold distance of the vertical line 208. For example, in FIG. 5, the vertical line 310 is positioned sufficiently close to the vertical line 208 such that the vertical line 310 is no longer separately visible from the vertical line 208. This may indicate that the anatomical structure 204 is centered with respect to the horizontal dimension of the ultrasound image 202.

Figure 6:
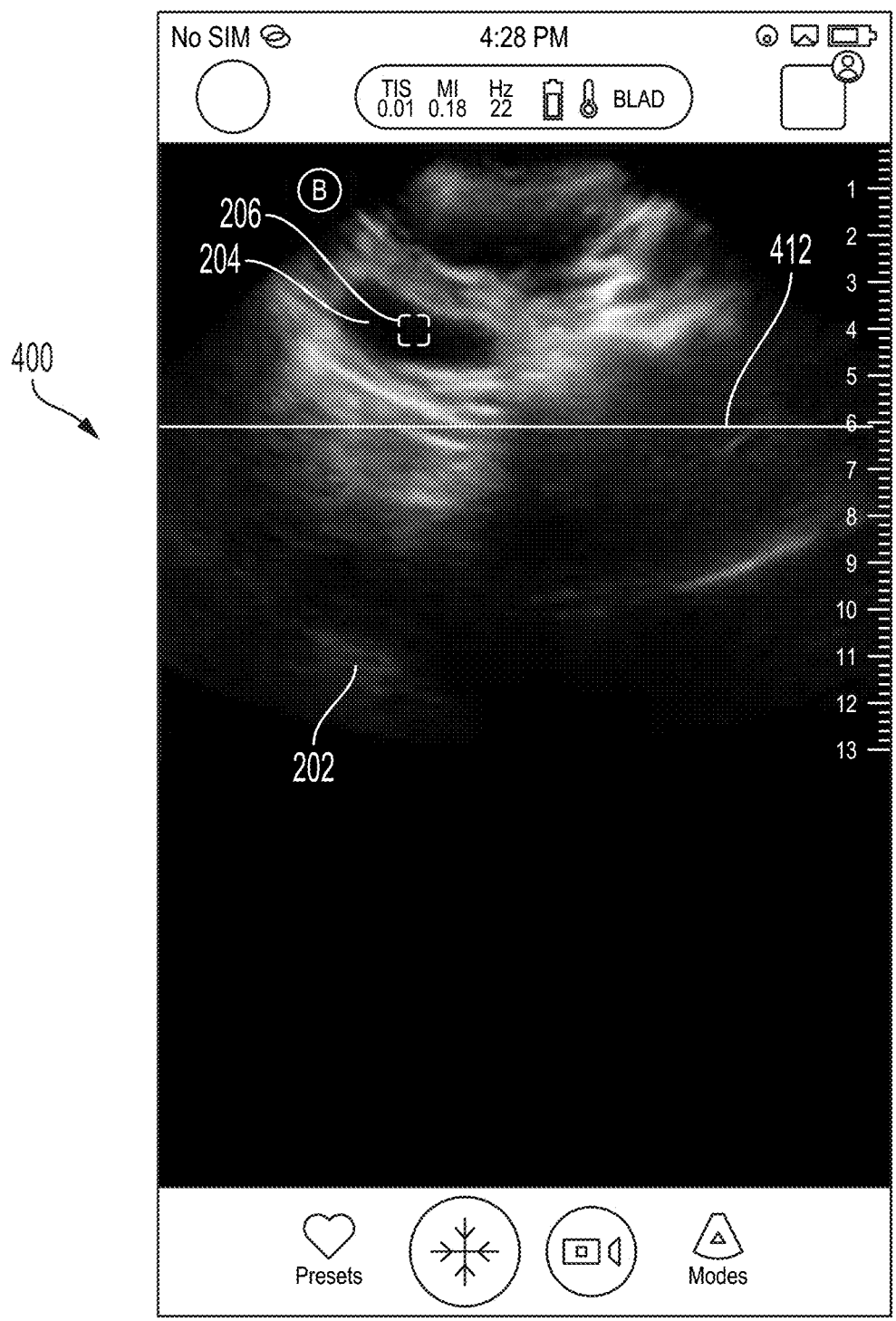
FIG. 6 illustrates another example graphical user interface (GUI) for collection of ultrasound images of an anatomical structure, in accordance with certain embodiments described herein.

FIG. 6 illustrates another example GUI 400, in accordance with certain embodiments described herein. The GUI 400 is the same as the GUI 200, except that the GUI 400 does not include the vertical line 208 and does include a horizontal line 412. The horizontal line 412 extends horizontally (i.e., horizontally with respect to the ultrasound image 202) through the ultrasound image 202 and is located halfway along the vertical dimension of the ultrasound image 202. In FIG. 6, the horizontal line 412 extends all the way through the ultrasound image 202, but in some embodiments the horizontal line 412 may extend through only a portion of the ultrasound image 202.

Displaying the symbol 206 may help the user position the ultrasound device such that the anatomical structure 204 is centered in the ultrasound image 202. As the user moves the ultrasound device, the position of the anatomical structure 204 in the ultrasound image 202 may change. Because in FIG. 6, the anatomical structure 204 is not positioned in the ultrasound image 202 such that the symbol 206 is positioned within a threshold distance of the horizontal line 412, this may indicate that the anatomical structure 204 is not centered with respect to the vertical dimension of the ultrasound image 202.

Figure 7:
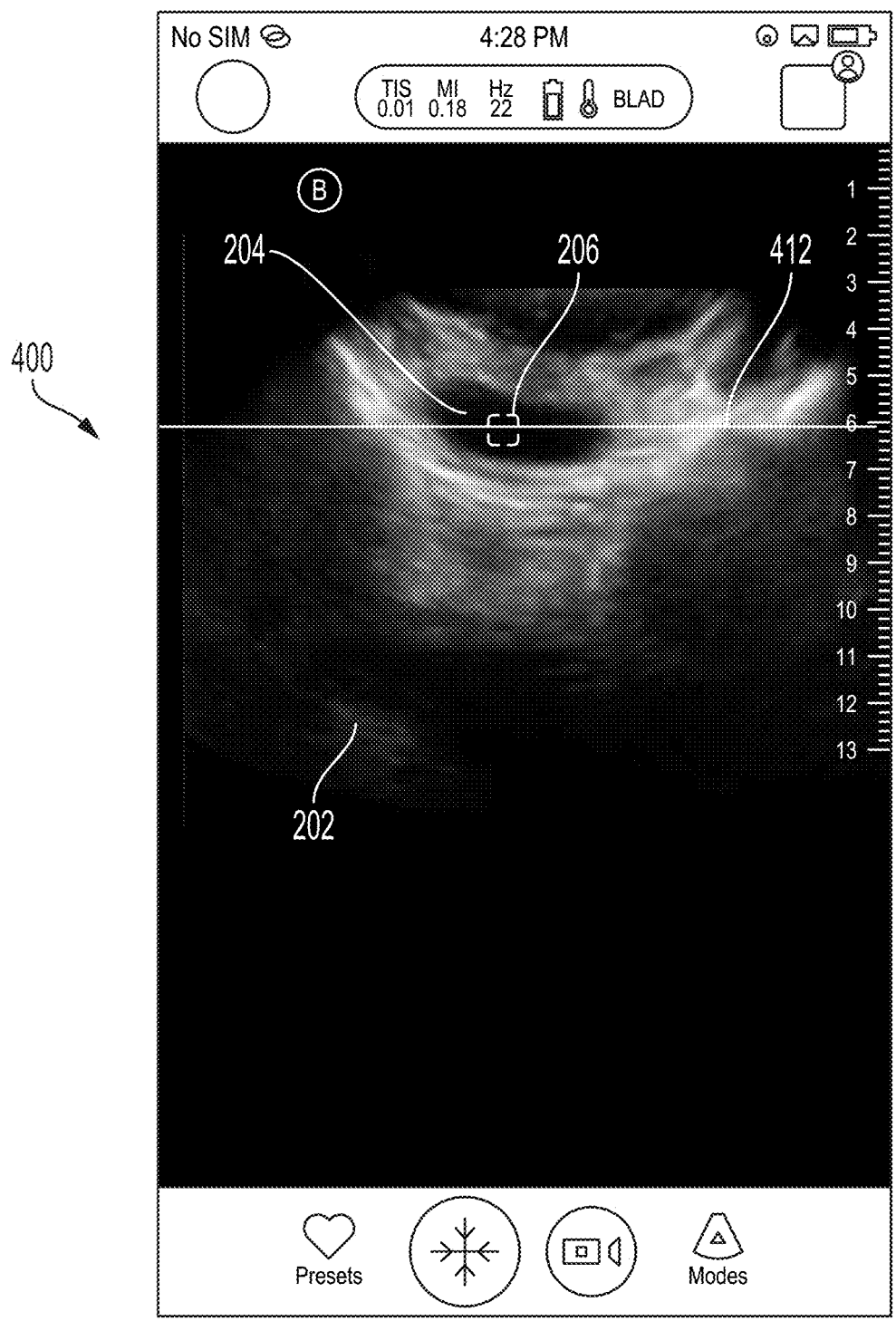
FIG. 7 illustrates another example of the GUI of FIG. 6, in accordance with certain embodiments described herein.

FIG. 7 illustrates another example of the GUI 400, in accordance with certain embodiments described herein. In FIG. 7, the anatomical structure 204 is positioned in the ultrasound image 202 such that the symbol 206 is positioned within a threshold distance of the horizontal line 412. This may indicate that the anatomical structure 204 is centered with respect to the vertical dimension of the ultrasound image 202.

Figure 8:
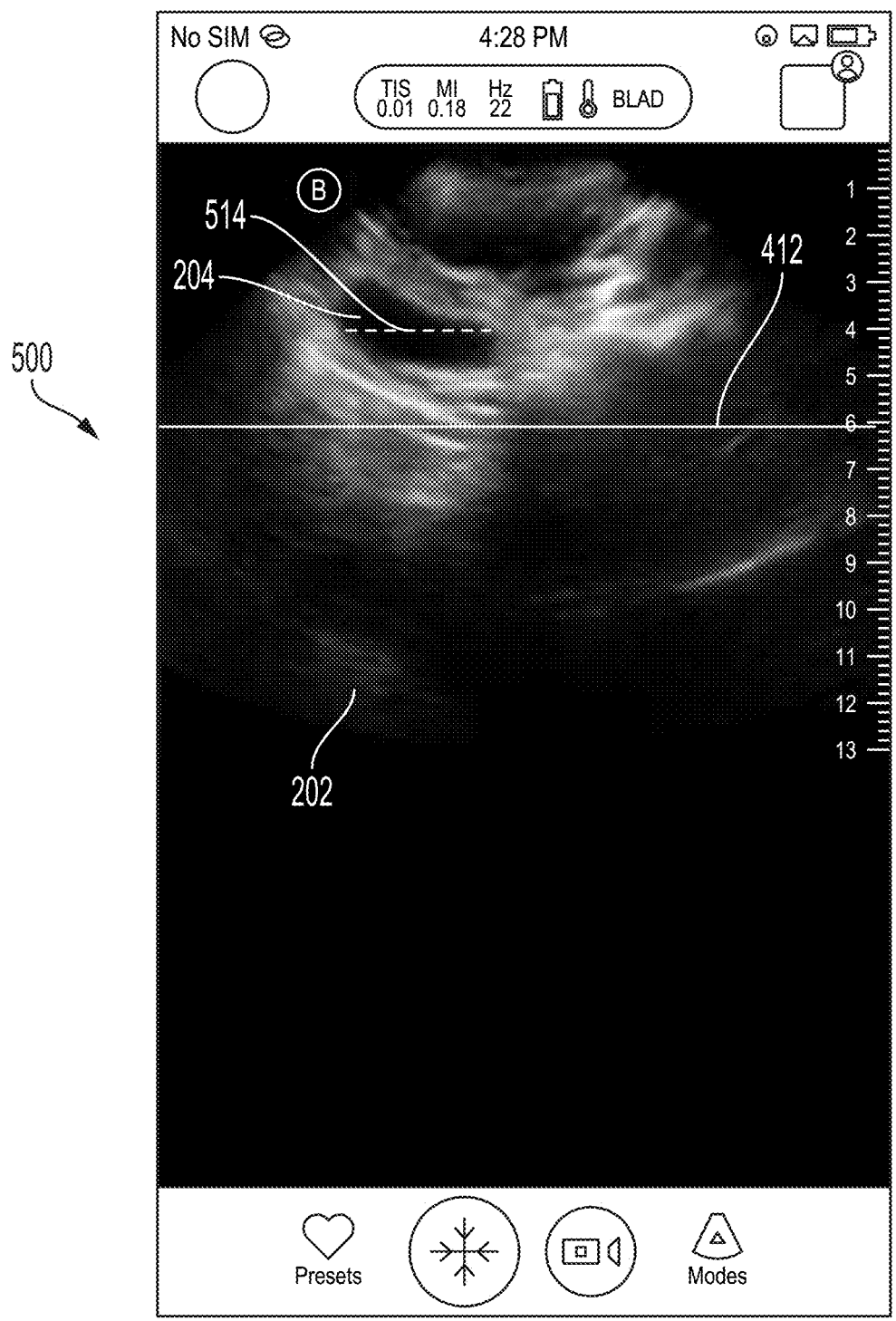
FIG. 8 illustrates another example graphical user interface (GUI) for collection of ultrasound images of an anatomical structure, in accordance with certain embodiments described herein.

FIG. 8 illustrates another example GUI 500, in accordance with certain embodiments described herein. The GUI 500 is the same as the GUI 400, except that the GUI 500 includes a horizontal line 514 and does not include the symbol 206. The horizontal line 514 is superimposed on the ultrasound image 202 and is an indicator of the location of a specific point on the anatomical structure 204. In FIG. 8, the horizontal line 514 is an indicator of the location of the centroid of the anatomical structure 204. In particular, the horizontal line 514 extends horizontally (i.e., horizontally with respect to the ultrasound image 202) from one edge of the anatomical structure 204, through the location of the centroid of the anatomical structure 204, and to the other edge of the anatomical structure 204. As the ultrasound device collects new ultrasound images that are displayed by the processing device, and the anatomical structure 204 is located at different locations on the ultrasound image 202, the processing device may reposition the horizontal line 514 such that the horizontal line 514 continues to extend horizontally from one edge of the anatomical structure 204, through the location of the centroid of the anatomical structure 204, and to the other edge of the anatomical structure 204. Further description of the horizontal line 514 may be found with reference to acts 104 and 106.

Displaying the horizontal line 514 may help the user position the ultrasound device such that the anatomical structure 204 is centered in the ultrasound image 202. As the user moves the ultrasound device, the position of the anatomical structure 204 in the ultrasound image 202 may change. Because in FIG. 8, the anatomical structure 204 is not positioned in the ultrasound image 202 such that the horizontal line 514 is positioned within a threshold distance of the horizontal line 412, this may indicate that the anatomical structure 204 is not centered with respect to the vertical dimension of the ultrasound image 202.

Figure 9:
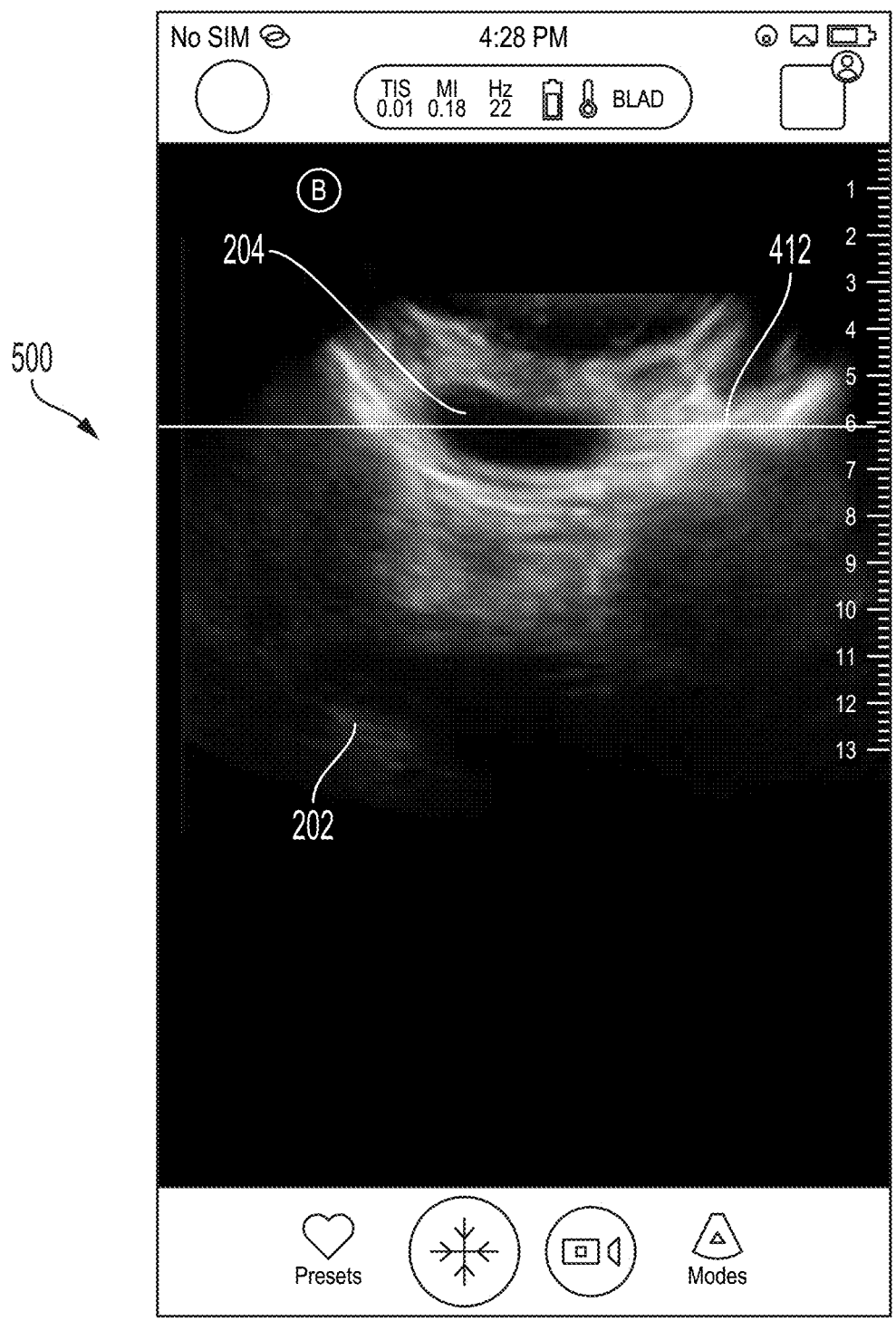
FIG. 9 illustrates another example of the GUI of FIG. 8, in accordance with certain embodiments described herein.

FIG. 9 illustrates another example of the GUI 500, in accordance with certain embodiments described herein. In FIG. 9, the anatomical structure 204 is positioned in the ultrasound image 202 such that the horizontal line 514 is positioned within a threshold distance of the horizontal line 412. For example, in FIG. 9, the horizontal line 514 is positioned sufficiently close to the horizontal line 412 such that the horizontal line 514 is no longer separately visible from the horizontal line 412. This may indicate that the anatomical structure 204 is centered with respect to the vertical dimension of the ultrasound image 202.

Figure 10:
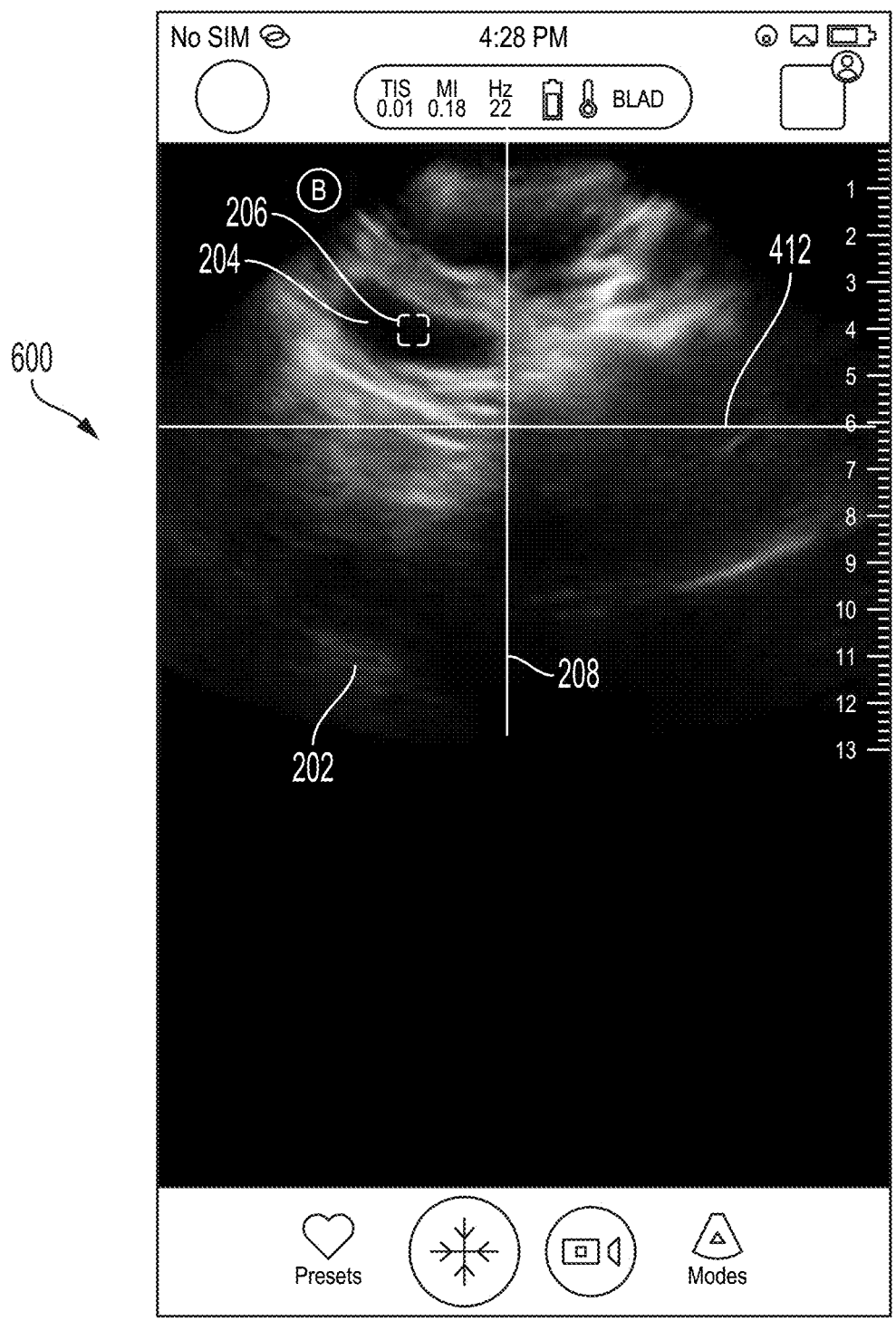
FIG. 10 illustrates another example graphical user interface (GUI) for collection of ultrasound images of an anatomical structure, in accordance with certain embodiments described herein.

FIG. 10 illustrates another example GUI 600, in accordance with certain embodiments described herein. The GUI 600 is the same as the GUI 400, except that the GUI 600 also includes the vertical line 208.

Displaying the symbol 206 may help the user position the ultrasound device such that the anatomical structure 204 is centered in the ultrasound image 202. As the user moves the ultrasound device, the position of the anatomical structure 204 in the ultrasound image 202 may change. Because in FIG. 10, the anatomical structure 204 is not positioned in the ultrasound image 202 such that the symbol 206 is positioned within a threshold distance of the intersection of the horizontal line 412 and the vertical line 208, this may indicate that the anatomical structure 204 is not centered with respect to the horizontal and vertical dimensions of the ultrasound image 202.

Figure 11:
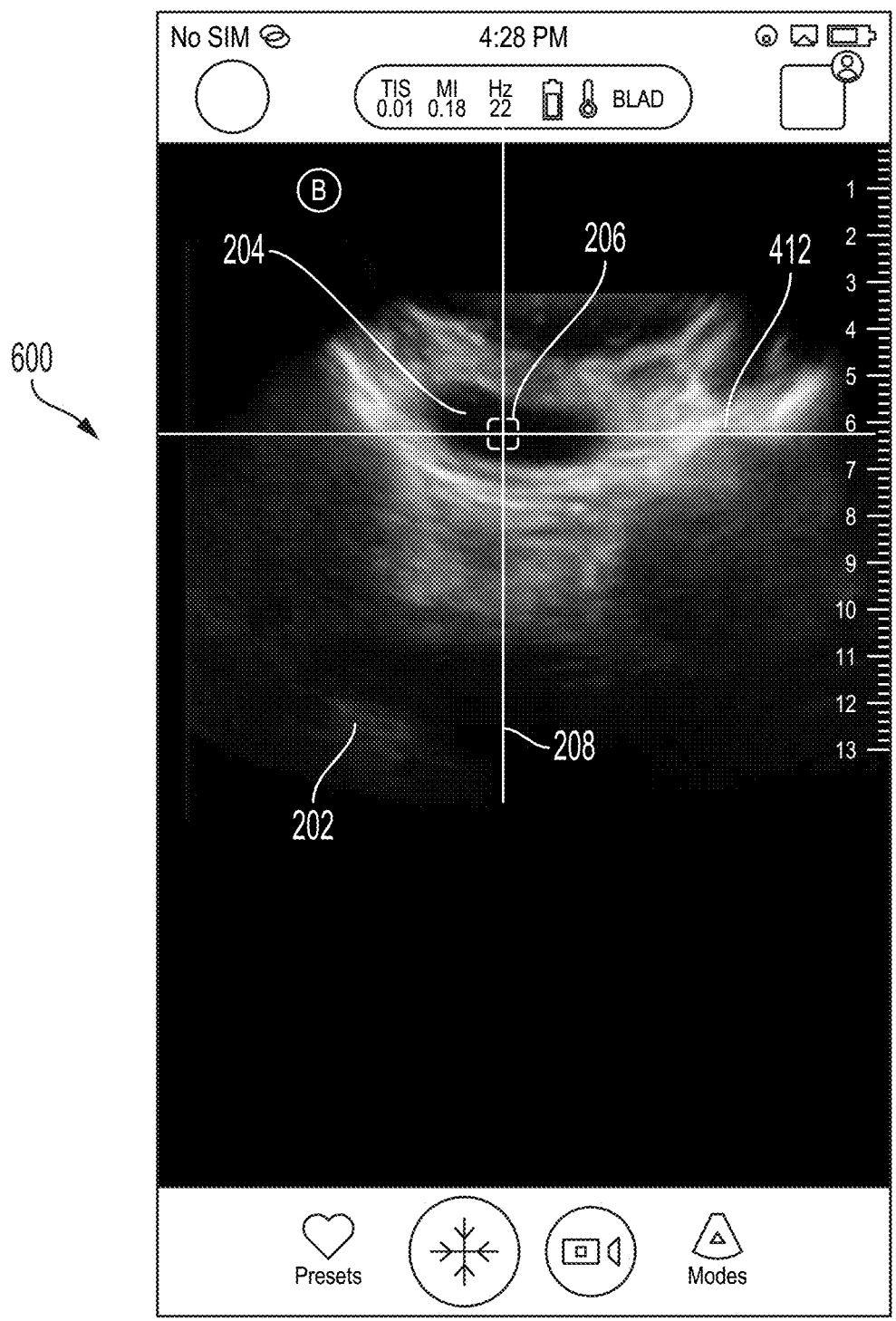
FIG. 11 illustrates another example of the GUI of FIG. 10, in accordance with certain embodiments described herein.

FIG. 11 illustrates another example of the GUI 600, in accordance with certain embodiments described herein. In FIG. 11, the anatomical structure 204 is positioned in the ultrasound image 202 such that the symbol 206 is positioned within a threshold distance of the intersection of the horizontal line 412 and the vertical line 208. This may indicate that the anatomical structure 204 is centered with respect to the horizontal and vertical dimensions of the ultrasound image 202.

Figure 12:
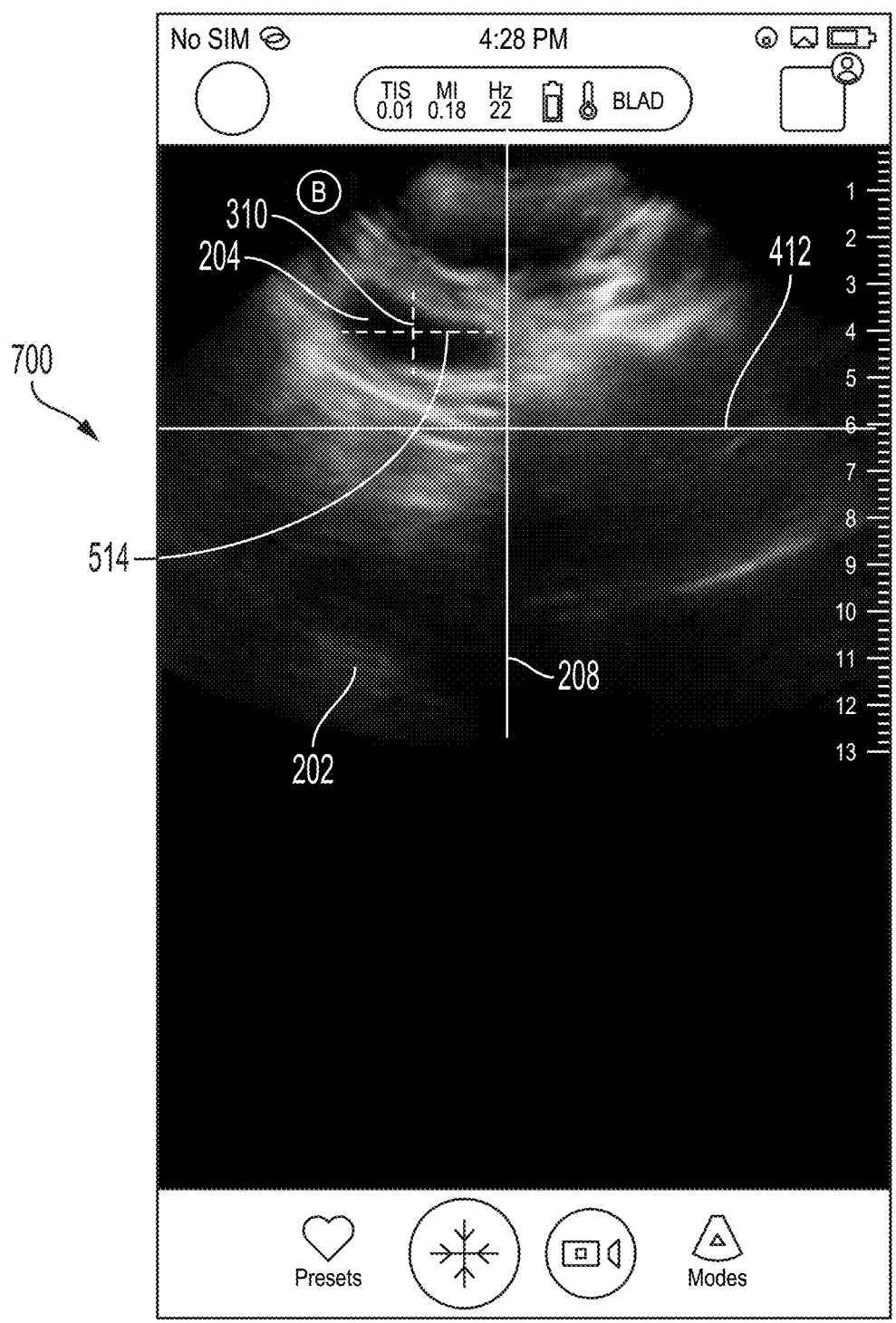
FIG. 12 illustrates another example graphical user interface (GUI) for collection of ultrasound images of an anatomical structure, in accordance with certain embodiments described herein.

FIG. 12 illustrates another example GUI 700, in accordance with certain embodiments described herein. The GUI 700 is the same as the GUI 600, except that the GUI 700 includes the vertical line 310 and the horizontal line 514 and lacks the symbol 206.

Displaying the vertical line 310 and the horizontal line 514 may help the user position the ultrasound device such that the anatomical structure 204 is centered in the ultrasound image 202. As the user moves the ultrasound device, the position of the anatomical structure 204 in the ultrasound image 202 may change. Because in FIG. 12, the anatomical structure 204 is not positioned in the ultrasound image 202 such that the vertical line 310 is positioned within a threshold distance of the vertical line 208 and the horizontal line 514 is positioned within a threshold distance of the horizontal line 412, this may indicate that the anatomical structure 204 is not centered with respect to the horizontal and vertical dimensions of the ultrasound image 202.

Figure 13:
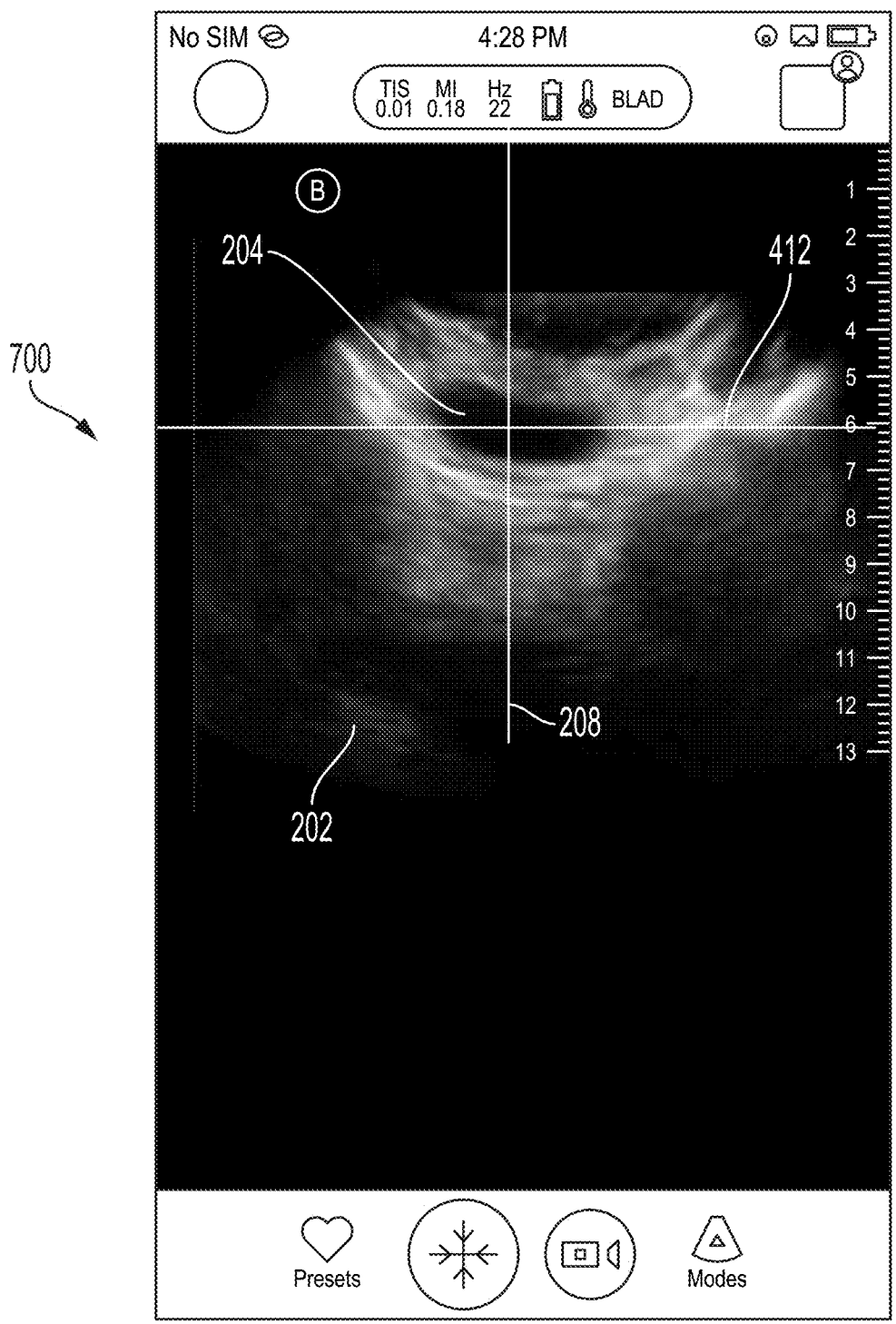
FIG. 13 illustrates another example of the GUI of FIG. 12, in accordance with certain embodiments described herein.

FIG. 13 illustrates another example of the GUI 700, in accordance with certain embodiments described herein. In FIG. 13, the anatomical structure 204 is positioned in the ultrasound image 202 such that the vertical line 310 is positioned within a threshold distance of the vertical line 208 and the horizontal line 514 is positioned within a threshold distance of the horizontal line 412. For example, in FIB. 13, the vertical line 310 is positioned sufficiently close to the vertical line 208 such that the vertical line 310 is no longer separately visible from the vertical line 208, and the horizontal line 514 is positioned sufficiently close to the horizontal line 412 such that the horizontal line 514 is no longer separately visible from the horizontal line 412. This may indicate that the anatomical structure 204 is centered with respect to the horizontal and vertical dimensions of the ultrasound image 202.

Figure 14:
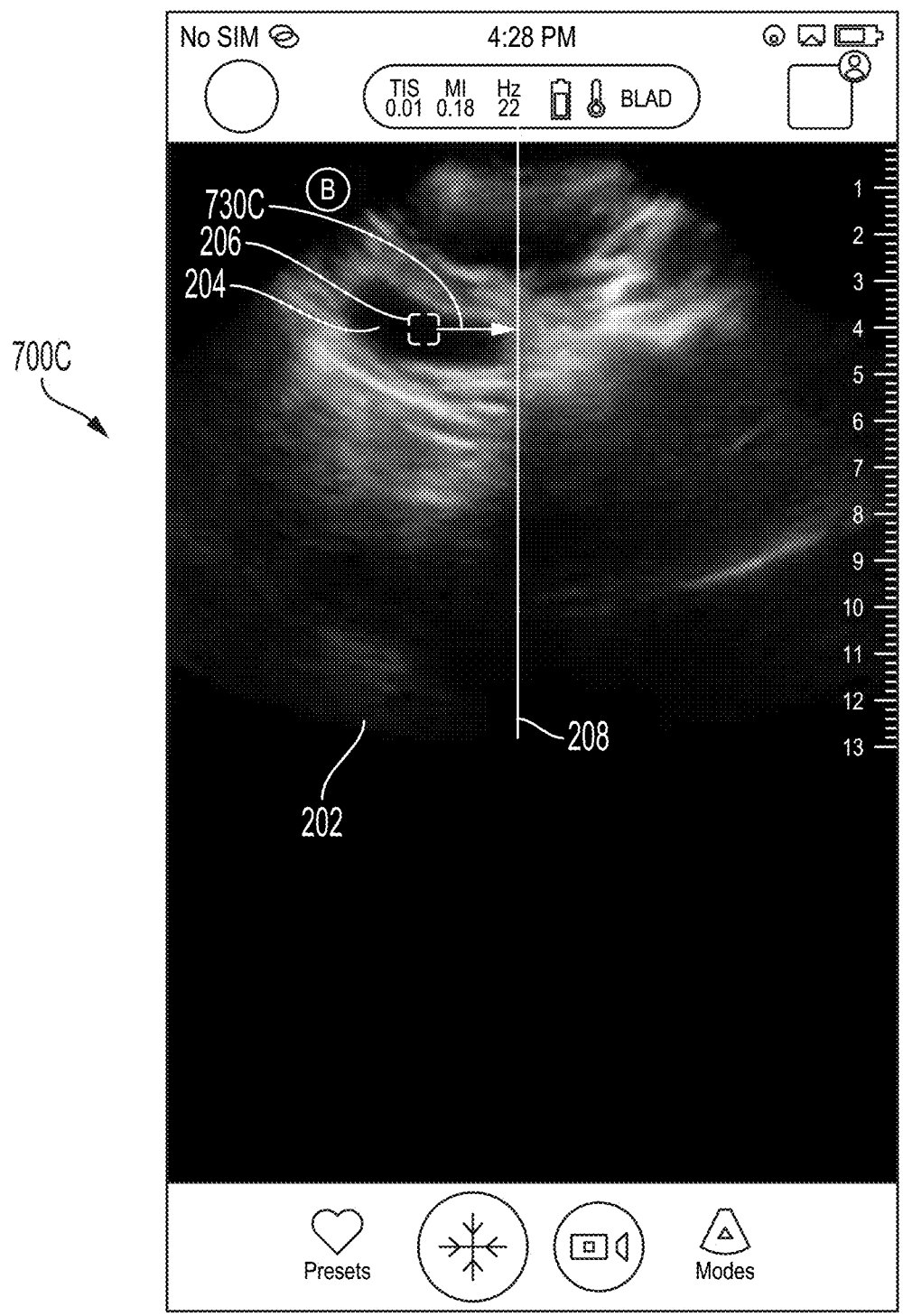
FIG. 14 illustrates another example GUI, in accordance with certain embodiments described herein.

FIG. 14 illustrates another example GUI 700C, in accordance with certain embodiments described herein. The GUI 700C is the same as the GUI 200, except that the GUI 700C includes an arrow 730C pointing horizontally from the symbol 206 to the vertical line 208. The arrow 730C may indicate that the user should move the ultrasound device such that the symbol 206 on the anatomical structure 204 moves closer to the vertical line 208. It should be appreciated that an arrow may be included in other GUIs described herein, for example, from the symbol 206 vertically to the horizontal line 412, from the symbol 206 diagonally to the intersection of the vertical line 208 and the horizontal line 412, from the vertical line 310 on the anatomical structure 204 horizontally to the vertical line 208, from the horizontal line 514 on the anatomical structure 204 vertically to the horizontal line 412, or from the intersection of the vertical line 310 and the horizontal line 514 to the intersection of the vertical line 208 and the horizontal line 412.

Figure 15:
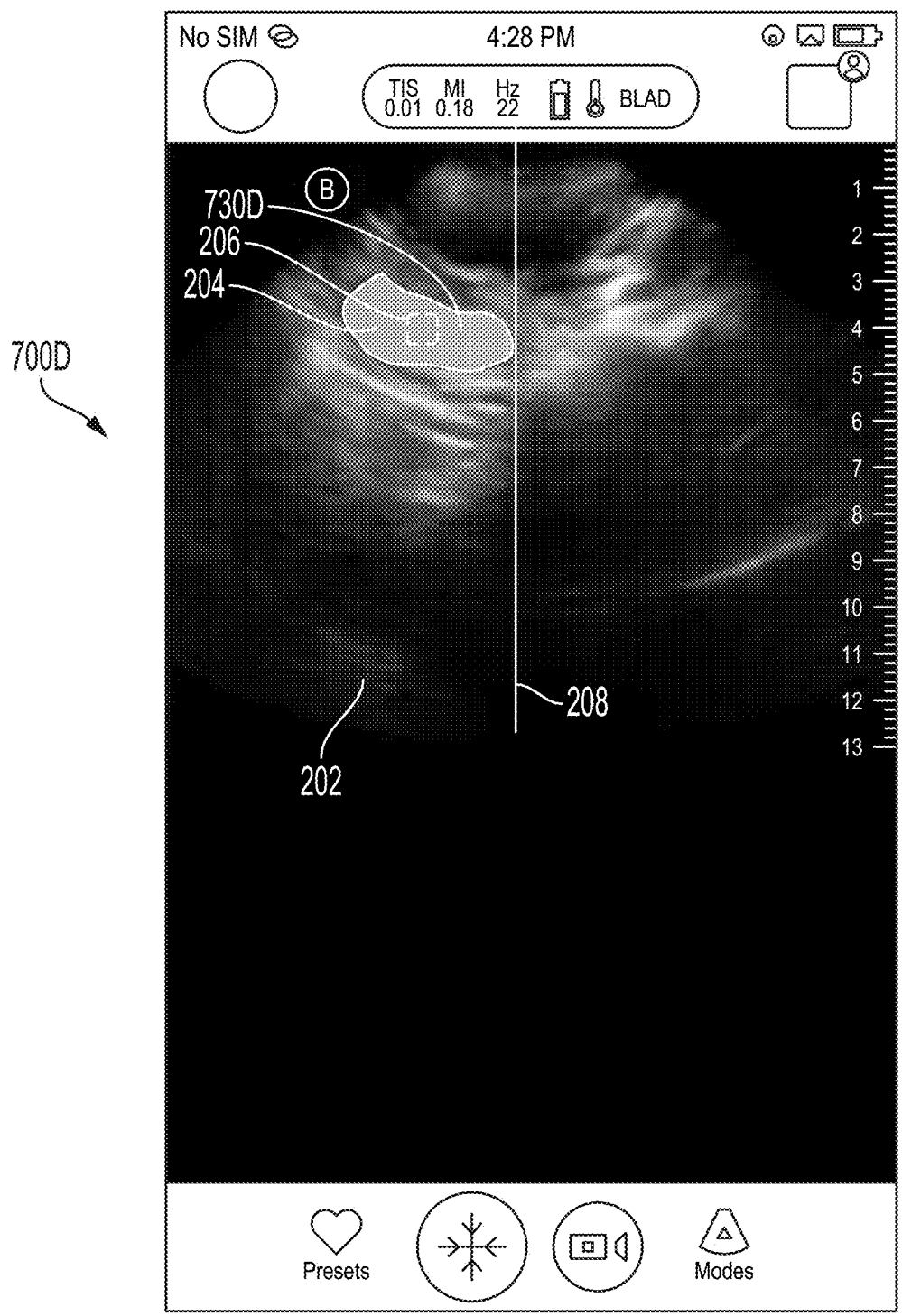
FIG. 15 illustrates another example GUI, in accordance with certain embodiments described herein.

FIG. 15 illustrates another example GUI 700D, in accordance with certain embodiments described herein. The GUI 700D is the same as the GUI 200, except that the GUI 700D includes a segmentation mask 730D. The segmentation mask 730D may be positioned over pixels determined to be in the interior of the anatomical structure 204. Further description of generating such a segmentation mask, for example by a statistical model, may be found above with reference to act 104. In some embodiments, the processing device may change the color of the segmentation mask 730D based on the distance from the symbol 206 on the anatomical structure 204 to the vertical line 208. For example, the processing device may change the color from red at far distances to green at near distances. In some embodiments, the processing device may change the saturation of the segmentation mask 730D based on the distance from the symbol 206 on the anatomical structure 204 to the vertical line 208. For example, the processing device may change the saturation from less saturated at far distances to more saturated at near distances. In some embodiments, the processing device may change the transparency of the segmentation mask 730D based on the distance from the symbol 206 on the anatomical structure 204 to the vertical line 208. For example, the processing device may change the transparency from very transparent at far distances to very opaque at near distances. In some embodiments, the processing device may change one or more of the color, the saturation, and the transparency of the segmentation mask 730D based on the distance from the symbol 206 on the anatomical structure 204 to the vertical line 208.

It should be appreciated that the processing device may change one or more of the color, the saturation, and the transparency of the segmentation mask 730D in other GUIs described herein, for example, based on the distance from the symbol 206 vertically to the horizontal line 412, from the symbol 206 diagonally to the intersection of the vertical line 208 and the horizontal line 412, from the vertical line 310 on the anatomical structure 204 horizontally to the vertical line 208, from the horizontal line 514 on the anatomical structure 204 vertically to the horizontal line 412, or from the intersection of the vertical line 310 and the horizontal line 514 to the intersection of the vertical line 208 and the horizontal line 412.

In some embodiments, the processing device may change the color of the symbol 206, the vertical line 310, and/or the horizontal line 514 based on its distance from the horizontal line 412, the vertical line 208, or from the intersection of the vertical line 208 and the horizontal line 412. In some embodiments, the processing device may change the color of the horizontal line 412 and/or the vertical line 208 based on their distance, or the distance of their intersection, from the symbol 206, the vertical line 310, and/or the horizontal line 514. For example, the processing device may change the color from red at far distances to green at near distances.

In some embodiments, a GUI may include both a symbol and either or both of a horizontal line and vertical line extending through the anatomical structure. In some embodiments in which the indicator is a symbol, the symbol may be sized based on how close it is desired for the specific point to be to the vertical line and/or the horizontal line extending through the ultrasound image. For example, the size of the symbol may be such that when the symbol touches the vertical line or horizontal line, the specific point is within the desired distance of the vertical line and/or the horizontal line.

Figure 16:
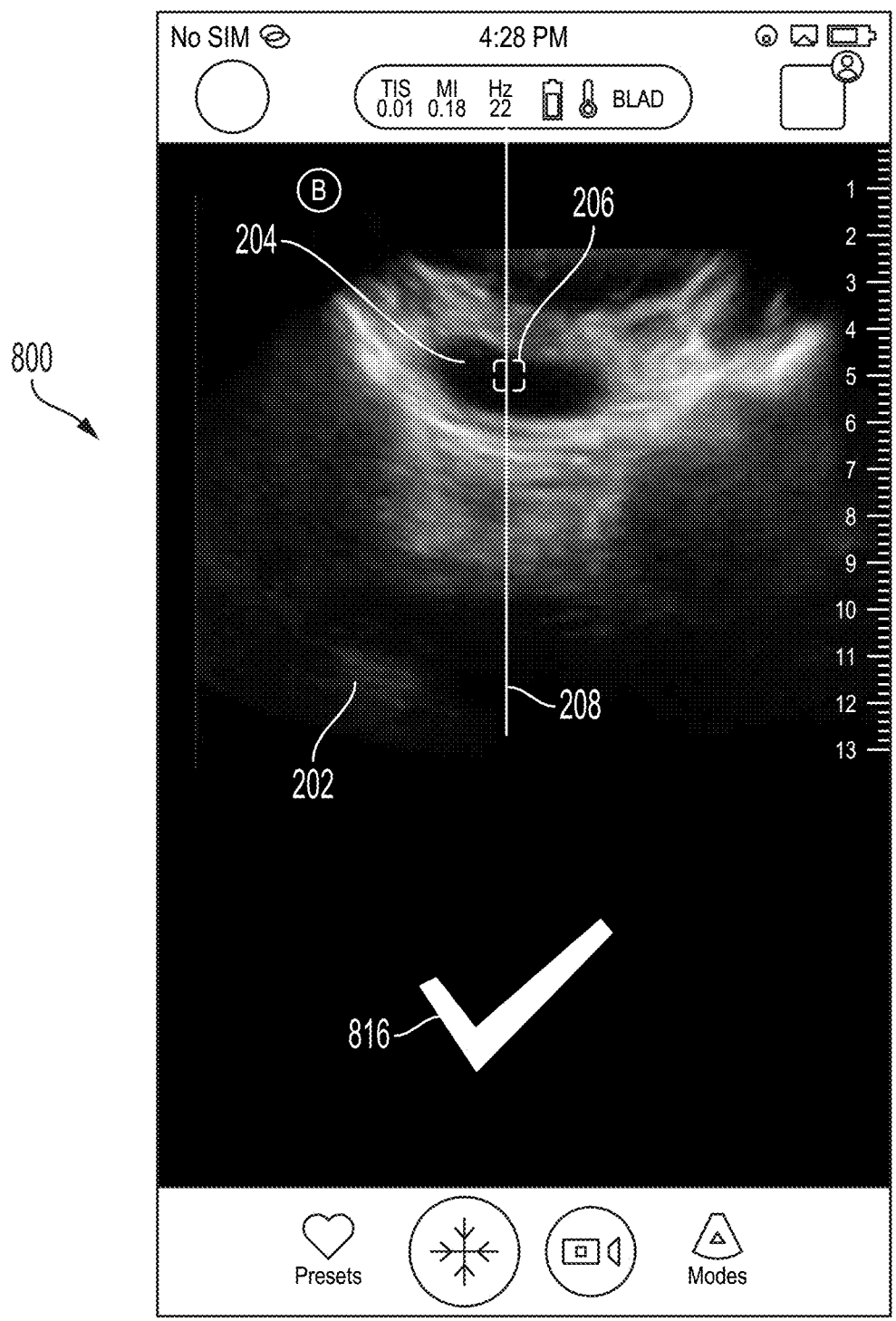
FIG. 16 illustrates another example GUI, in accordance with certain embodiments described herein.

FIG. 16 illustrates another example GUI 800, in accordance with certain embodiments described herein. The GUI 800 is the same as the GUI 200, except that the GUI 800 includes a second indicator 816. In some embodiments, the processing device may display the second indicator 816 when the symbol 206 is within a threshold distance of the vertical line 208. While in FIG. 16, the second indicator 816 is a checkmark, the second indicator 816 may have other forms, such as a different symbol, or text. Additionally, the processing device may display the second indicator 816 when other types of indicators, such as the vertical line 310 and the horizontal line 514, are within a threshold distance or either of both of the vertical line 208 and the horizontal line 412.

Figure 17:
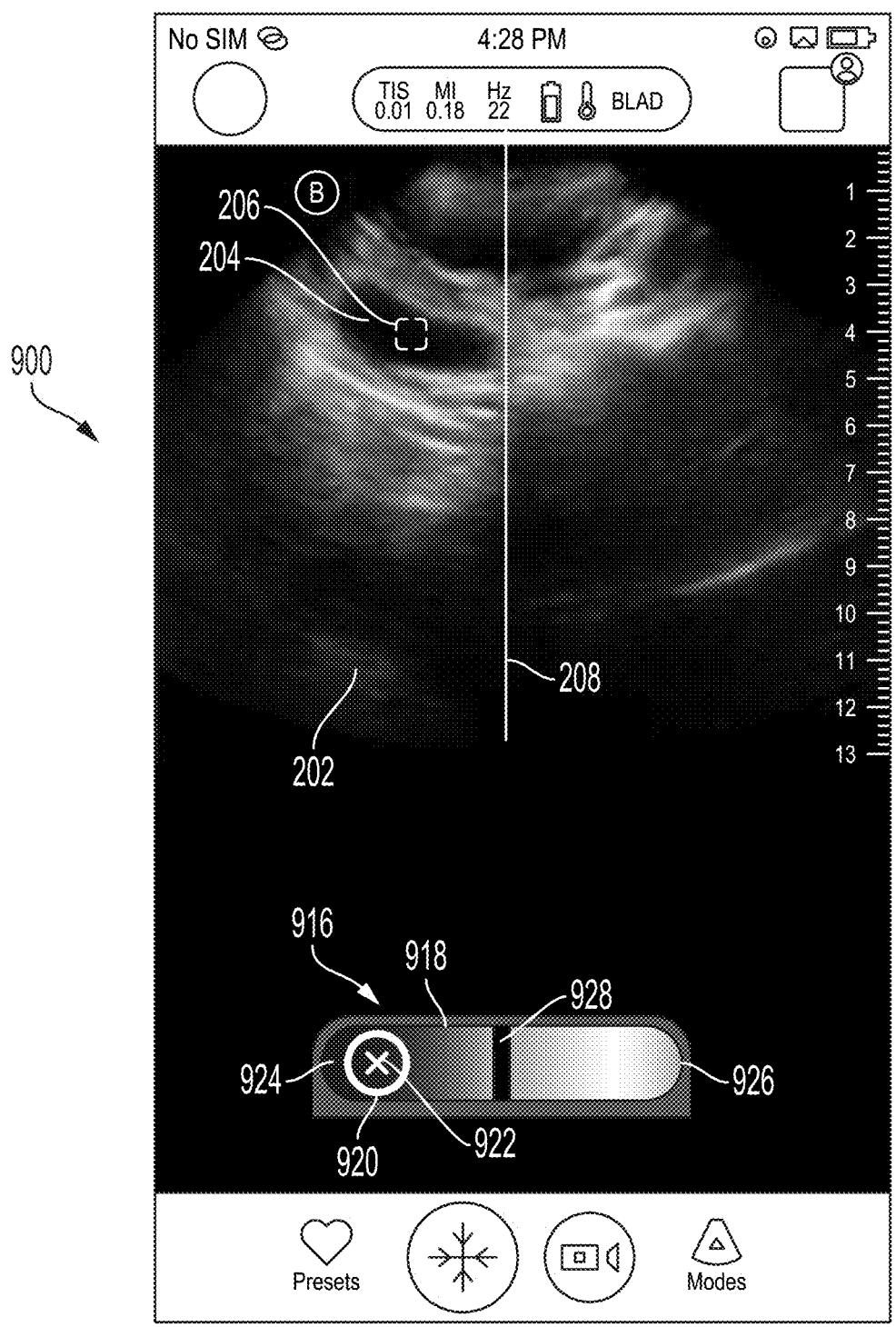
FIG. 17 illustrates another example GUI, in accordance with certain embodiments described herein.

FIG. 17 illustrates another example GUI 900, in accordance with certain embodiments described herein. The GUI 900 is the same as the GUI 900, except that the GUI 900 includes a second indicator 916. The second indicator 916 includes a frame 918 and a slider 920. The frame includes a first end 924, a second end 926, and a threshold indicator 928. The slider 920 includes a symbol 922. In some embodiments, the second indicator 916 may indicate how close the symbol 206 is to the vertical line 208. For example, the ratio of the distance of the slider 920 from the first end 924 to the total length of the frame from the first end 924 to the second end 926 may be proportional to how close the symbol 206 is to the vertical line 208. In some embodiments, when the slider 920 is beyond the threshold indicator 928, this may indicate that the symbol 206 is within a threshold distance of the vertical line 208. In some embodiments, the symbol 920 may have one form (e.g., an "x") when the slider 920 is on one side of the threshold indicator 928 and another form (e.g., a checkmark) when the slider 920 is on the other side of the threshold indicator 928. In some embodiments, the frame 918 may have a color that varies along its length. For example, the frame 918 may have more reddish colors near the first end 924 and more greenish colors near the second end 926. When the slider 920 is located at a greener portion of the frame 918, this may indicate that the symbol 206 is closer to the vertical line 208 than when the slider 920 is located at a redder portion of the frame 918. The processing device may display the second indicator 916 such that it behaves the same way as described above for other types of indicators, such as the vertical line 310 and the horizontal line 514, and for either or both of the vertical line 208 and the horizontal line 412.

While the above description has used the bladder as an exemplary anatomical structure, the methods and apparatuses described herein may also be applied to collecting ultrasound images of the thyroid, the abdominal aorta, a superficial artery, the brain (e.g., a neonatal brain), the liver, the breast, the kidney, the thyroid, and amniotic fluid. Example applications include venous access identification when imaging a superficial artery; imaging benign hemangiomas in the liver; imaging nodules in the thyroid, imaging cancerous tumors in the liver, breast, kidney, and pancreas to detect changes over time; and amniotic fluid evaluation.

Figure 18:
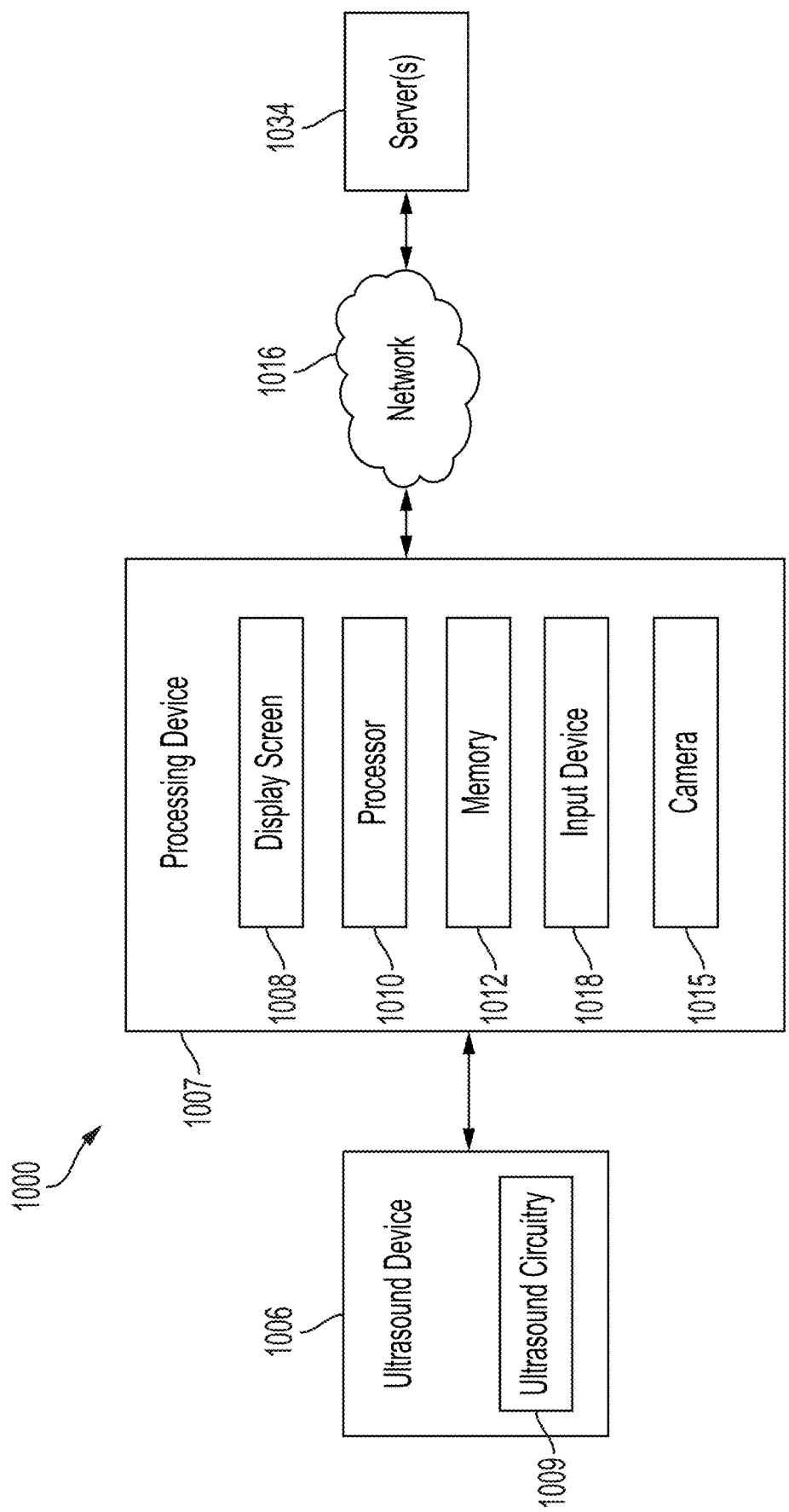
FIG. 18 illustrates a schematic block diagram of an example ultrasound system upon which various aspects of the technology described herein may be practiced.

FIG. 18 illustrates a schematic block diagram of an example ultrasound system 1000 upon which various aspects of the technology described herein may be practiced. The ultrasound system 1000 includes an ultrasound device 1006, a processing device 1007, a network 1016, and one or more servers 1034.

The ultrasound device 1006 includes ultrasound circuitry 1009. The processing device 1007 includes a camera 1015, a display screen 1008, a processor 1010, a memory 1012, and an input device 1018. The processing device 1007 is in wired (e.g., through a lightning connector or a mini-USB connector) and/or wireless communication (e.g., using BLUETOOTH®, ZIGBEE, and/or WiFi wireless protocols) with the ultrasound device 1006. The processing device 1007 is in wireless communication with the one or more servers 1034 over the network 1016. However, the wireless communication with the processing device 1034 is optional.

The ultrasound device 1006 may be configured to generate ultrasound data that may be employed to generate an ultrasound image. The ultrasound device 1006 may be constructed in any of a variety of ways. In some embodiments, the ultrasound device 1006 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. The ultrasound circuitry 1009 may be configured to generate the ultrasound data. The ultrasound circuitry 1009 may include one or more ultrasonic transducers monolithically integrated onto a single semiconductor die. The ultrasonic transducers may include, for example, one or more capacitive micromachined ultrasonic transducers (CMUTs), one or more CMOS (complementary metal-oxide-semiconductor) ultrasonic transducers (CUTs), one or more piezoelectric micromachined ultrasonic transducers (PMUTs), and/or one or more other suitable ultrasonic transducer cells. In some embodiments, the ultrasonic transducers may be formed the same chip as other electronic components in the ultrasound circuitry 1009 (e.g., transmit circuitry, receive circuitry, control circuitry, power management circuitry, and processing circuitry) to form a monolithic ultrasound device. The ultrasound device 1006 may transmit ultrasound data and/or ultrasound images to the processing device 1007 over a wired (e.g., through a lightning connector or a mini-USB connector) and/or wireless (e.g., using BLUETOOTH®, ZIGBEE, and/or WiFi wireless protocols) communication link.

Referring now to the processing device 1007, the processor 1010 may include specially-programmed and/or special-purpose hardware such as an application-specific integrated circuit (ASIC). For example, the processor 1010 may include one or more graphics processing units (GPUs) and/or one or more tensor processing units (TPUs). TPUs may be ASICs specifically designed for machine learning (e.g., deep learning). The TPUs may be employed to, for example, accelerate the inference phase of a neural network. The processing device 1007 may be configured to process the ultrasound data received from the ultrasound device 1006 to generate ultrasound images for display on the display screen 1008. The processing may be performed by, for example, the processor 1010. The processor 1010 may also be adapted to control the acquisition of ultrasound data with the ultrasound device 1006. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

The processing device 1007 may be configured to perform certain of the processes (e.g., the process 100) described herein using the processor 1010 (e.g., one or more computer hardware processors) and one or more articles of manufacture that include non-transitory computer-readable storage media such as the memory 1012. The processor 1010 may control writing data to and reading data from the memory 1012 in any suitable manner. To perform certain of the processes described herein, the processor 1010 may execute one or more processor-executable instructions stored in one or more non-transitory computer-readable storage media (e.g., the memory 1012), which may serve as non-transitory computer-readable storage media storing processor-executable instructions for execution by the processor 1010. The camera 1015 may be configured to detect light (e.g., visible light) to form an image. The camera 1015 may be on the same face of the processing device 1007 as the display screen 1008. The display screen 1008 may be configured to display images and/or videos, and may be, for example, a liquid crystal display (LCD), a plasma display, and/or an organic light emitting diode (OLED) display on the processing device 1007. The input device 1018 may include one or more devices capable of receiving input from a user and transmitting the input to the processor 1010. For example, the input device 1018 may include a keyboard, a mouse, a microphone, touch-enabled sensors on the display screen 1008, and/or a microphone. The display screen 1008, the input device 1018, and the camera 1015 may be communicatively coupled to the processor 1010 and/or under the control of the processor 1010.

It should be appreciated that the processing device 1007 may be implemented in any of a variety of ways. For example, the processing device 1007 may be implemented as a handheld device such as a mobile smartphone or a tablet. Thereby, a user of the ultrasound device 1006 may be able to operate the ultrasound device 1006 with one hand and hold the processing device 1007 with another hand. In other examples, the processing device 1007 may be implemented as a portable device that is not a handheld device, such as a laptop. In yet other examples, the processing device 1007 may be implemented as a stationary device such as a desktop computer. The processing device 1007 may be connected to the network 1016 over a wired connection (e.g., via an Ethernet cable) and/or a wireless connection (e.g., over a WiFi network). The processing device 1007 may thereby communicate with (e.g., transmit data to) the one or more servers 1034 over the network 1016. For further description of ultrasound devices and systems, see U.S. patent application Ser. No. 15/415,434 titled "UNIVERSAL ULTRASOUND DEVICE AND RELATED APPARATUS AND METHODS," filed on Jan. 25, 2017 and published as U.S. Pat. App. Publication No. 2017-0360397 A1 (and assigned to the assignee of the instant application), which is incorporated herein by reference in its entirety.

FIG. 18 should be understood to be non-limiting. For example, the ultrasound system 1000 may include fewer or more components than shown and the processing device 1007 may include fewer or more components than shown.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Various inventive concepts may be embodied as one or more processes, of which an example has been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. A method, comprising:
receiving an ultrasound image;
automatically determining a location of a centroid of an anatomical structure depicted in the ultrasound image;
automatically determining an area of the anatomical structure depicted in the ultrasound image;
superimposing an indicator comprising a graphical symbol on the ultrasound image at the location of the centroid of the anatomical structure depicted in the ultrasound image; and
superimposing, on the ultrasound image, a transparent mask indicating the area of the anatomical structure;
wherein at least one of automatically determining the location of the centroid or automatically determining the area of the anatomical structure is performed using a statistical model trained from a plurality of training ultrasound images.

2. The method of claim 1, wherein the anatomical structure comprises a bladder.

3. The method of claim 1, wherein automatically determining the location of the centroid of the anatomical structure depicted in the ultrasound image further comprises using information about pixels in the training ultrasound images corresponding to respective centroids of anatomical structures in the training ultrasound images.

4. The method of claim 1, wherein the mask comprises a transparency value between fully transparent and fully opaque such that of at least a subset of pixels corresponding to the anatomical structure are viewable through the mask.

5. The method of claim 1, wherein the indicator comprises an open symbol having an outline, the outline defining an opening therein, and wherein superimposing the indicator on the ultrasound image comprises superimposing the indicator transparently at the location of the centroid of the anatomical structure depicted in the ultrasound image such that a subset of pixels corresponding to the anatomical structure in the ultrasound image are viewable through the opening of the open symbol.

6. The method of claim 1, wherein receiving, automatically determining and superimposing are performed on a processing device in operative communication with an ultrasound device, and wherein receiving the ultrasound image comprises receiving the ultrasound image from the ultrasound device.

7. The method of claim 1, wherein superimposing the indicator on the ultrasound image comprises displaying the indicator and the ultrasound image simultaneously on a display of a smartphone or tablet, wherein the smartphone or the tablet is further configured to operatively communicate with an ultrasound device and receive the ultrasound image from the ultrasound device.

8. The method of claim 1, wherein superimposing the indicator on the ultrasound image comprises displaying a vertical line extending from one edge of the anatomical structure, through the centroid of the anatomical structure, and to another edge of the anatomical structure.

9. The method of claim 1,
wherein receiving the ultrasound image comprises receiving the ultrasound image at a processing device from an ultrasound device, wherein the processing device is in operative communication with the ultrasound device; and
wherein the method further comprises, at the processing device, superimposing a vertical line on the ultrasound image, the vertical line positioned halfway across a horizontal dimension of the ultrasound image, wherein a distance between the indicator and the vertical line indicates a degree of centeredness of the anatomical structure in the ultrasound image for guiding movement of the ultrasound device in capturing a subsequent ultrasound image.

10. The method of claim 1, wherein the indicator is a first indicator, and wherein the method further comprises displaying a second indicator indicating a closeness in distance between the location of the centroid on the anatomical structure and a vertical line positioned halfway across a horizontal dimension of the ultrasound image.

11. The method of claim 1, further comprising capturing the ultrasound image from a handheld ultrasound device.

12. An apparatus, comprising:
processing circuitry configured to:
receive an ultrasound image;
automatically determine a location of a centroid of an anatomical structure depicted in the ultrasound image;
automatically determine an area of the anatomical structure depicted in the ultrasound image;
superimpose an indicator comprising a graphical symbol on the ultrasound image at the location of the centroid of the anatomical structure depicted in the ultrasound image; and
superimpose, on the ultrasound image, a transparent mask indicating the area of the anatomical structure;
wherein the processing circuitry is configured to at least one of automatically determine the location of the centroid or automatically determine the area of the anatomical structure using a statistical model trained from a plurality of training ultrasound images.

13. The apparatus of claim 12, wherein the anatomical structure comprises a bladder.

14. The apparatus of claim 12, wherein the processing circuitry is further configured, when automatically determining the location of the centroid of the anatomical structure depicted in the ultrasound image, to use information about pixels in the training ultrasound images corresponding to respective centroids of anatomical structures in the training ultrasound images.

15. The apparatus of claim 12, wherein the mask comprises a transparency value between fully transparent and fully opaque such that at least a subset of pixels corresponding to the anatomical structure are viewable through the mask.

16. The apparatus of claim 12, wherein the indicator comprises an open symbol having an outline, the outline defining an opening therein, and wherein the processing circuitry is configured, when superimposing the indicator on the ultrasound image, to superimpose the indicator transparently at the location of the centroid of the anatomical structure depicted in the ultrasound image such that a subset of pixels corresponding to the anatomical structure in the ultrasound image are viewable through the opening of the open symbol.

17. The apparatus of claim 12, wherein the processing circuitry is configured to receive the ultrasound image from an ultrasound device.

18. The apparatus of claim 12, wherein the processing circuitry is configured, when superimposing the indicator on the ultrasound image, to display the indicator and the ultrasound image simultaneously on a display of a smartphone or tablet, wherein the smartphone or the tablet is further configured to operatively communicate with an ultrasound device and receive the ultrasound image from the ultrasound device.

19. The apparatus of claim 12, wherein the processing circuitry is configured, when superimposing the indicator on the ultrasound image, to display a vertical line extending from one edge of the anatomical structure, through the centroid of the anatomical structure, and to a second edge of the anatomical structure.

20. The apparatus of claim 12, further comprising an ultrasound device configured to capture the ultrasound image, wherein the processing circuitry is further configured to:
   operatively communicate with the ultrasound device and receive the ultrasound image from the ultrasound device; and
   superimpose a vertical line on the ultrasound image, the vertical line positioned halfway across a horizontal dimension of the ultrasound image, wherein a distance in pixels between the indicator and the vertical line indicates a degree of centeredness of the anatomical structure in the ultrasound image for guiding movement of the ultrasound device in capturing a subsequent ultrasound image.

21. The apparatus of claim 12, wherein the indicator is a first indicator, and wherein the processing circuitry is further configured to display a second indicator indicating a closeness in distance between the location of the centroid on the anatomical structure and a vertical line positioned halfway across a horizontal dimension of the ultrasound image.

22. The apparatus of claim 12, wherein the processing circuitry is further configured to receive the ultrasound image from a handheld ultrasound device coupled to the processing circuitry.

* * * * *